United States Patent
Thomas et al.

(10) Patent No.: US 11,393,577 B2
(45) Date of Patent: Jul. 19, 2022

(54) MACHINE-LEARNING AND COMBINATORIAL OPTIMIZATION FRAMEWORK FOR MANAGING TASKS OF A DYNAMIC SYSTEM WITH LIMITED RESOURCES

(71) Applicant: General Electric Company, Schenectady, NY (US)

(72) Inventors: Bex George Thomas, Laguna Niguel, CA (US); Andrew Day, Newton, PA (US); Savanoor Pradeep Rai, Naperville, IL (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 453 days.

(21) Appl. No.: 16/456,297

(22) Filed: Jun. 28, 2019

(65) Prior Publication Data

US 2020/0411168 A1   Dec. 31, 2020

(51) Int. Cl.
  *G16H 40/20*    (2018.01)
  *G16H 50/20*    (2018.01)
  *G06Q 10/06*    (2012.01)

(52) U.S. Cl.
  CPC ......... *G16H 40/20* (2018.01); *G06Q 10/0631* (2013.01); *G06Q 10/06311* (2013.01); *G16H 50/20* (2018.01)

(58) Field of Classification Search
  CPC ............. G16H 40/20; G06Q 10/06312; G06Q 10/0633; G06Q 10/06311; G06Q 10/103; G06Q 10/063114
  See application file for complete search history.

(56) References Cited

U.S. PATENT DOCUMENTS 9,928,342 B1 * 3/2018 LaBorde ............. A61B 5/6852
2007/0129983 A1   6/2007 Scherpbier
(Continued)

FOREIGN PATENT DOCUMENTS

WO    2013067067 A3    5/2013

OTHER PUBLICATIONS

R. Yang, X. Ouyang, Y. Chen, P. Townend and J. Xu, "Intelligent Resource Scheduling at Scale: A Machine Learning Perspective," 2018 IEEE Symposium on Service-Oriented System Engineering (SOSE), 2018, pp. 132-141, doi: 10.1109/SOSE.2018.00025. (Year: 2018).*

(Continued)

*Primary Examiner* — Joseph D Burgess
(74) *Attorney, Agent, or Firm* — Amin, Turocy & Watson, LLP

(57) ABSTRACT

Techniques are described for managing tasks of a dynamic system with limited resources using a machine-learning and combinatorial optimization framework. In one embodiment, a computer-implemented method is provided that comprises employing, by a system operatively coupled to a processor, one or more first machine learning models to determine a total demand for tasks of a dynamic system within a defined time frame based on state information regarding a current state of the dynamic system, wherein the state information comprises task information regarding currently pending tasks of the tasks. The method further comprises, employing, by the system, one or more second machine learning models to determine turnaround times for completing the tasks based on the state information, and determining, by the system, a prioritization order for performing the currently pending tasks based on the total demand and the turnaround times.

30 Claims, 14 Drawing Sheets

(56) References Cited

U.S. PATENT DOCUMENTS

| | | | | |
|---|---|---|---|---|
| 2009/0119142 | A1* | 5/2009 | Yenni | H04L 67/12 |
| | | | | 705/7.15 |
| 2011/0010087 | A1* | 1/2011 | Wons | G06Q 10/06 |
| | | | | 701/533 |
| 2011/0125539 | A1* | 5/2011 | Bollapragada | G06Q 10/043 |
| | | | | 705/7.12 |
| 2013/0124220 | A1 | 5/2013 | Jourdan et al. | |
| 2014/0108033 | A1* | 4/2014 | Akbay | G16Z 99/00 |
| | | | | 705/2 |
| 2015/0066529 | A1* | 3/2015 | Lattuca | G16H 40/20 |
| | | | | 705/2 |
| 2016/0371441 | A1 | 12/2016 | Day | |
| 2017/0364642 | A1 | 12/2017 | Bogdanowicz et al. | |

OTHER PUBLICATIONS

International Application No. PCT/US2020/038886 filed Jun. 22, 2020—International Search Report and Written Opinion dated May 10, 2020; 12 pages.

International Preliminary Report on Patentability received for PCT Application Serial No. PCT/US2020/038886 dated Jan. 6, 2022, 9 pages.

\* cited by examiner

MACHINE-LEARNING AND COMBINATORIAL OPTIMIZATION FRAMEWORK FOR MANAGING TASKS OF A DYNAMIC SYSTEM WITH LIMITED RESOURCES

TECHNICAL FIELD

This application relates to computer-implemented techniques for managing tasks of a dynamic system with limited resources using a machine-learning and combinatorial optimization framework.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide for managing tasks of a dynamic system with limited resources using a machine-learning and combinatorial optimization framework. In various embodiments, the dynamic system comprises a medical care facility system (e.g., a hospital) and the disclosed systems, computer-implemented methods, apparatus and/or computer program products facilitate managing housekeeping services (also referred to as environmental services (EVS)) tasks of the medical care facility system to minimize turnaround times (TATs), meet service level requirements and subsequently reduce wait times for dirty beds by combining diagnostic analytics, machine learning and combinatorial optimization.

According to an embodiment, a system is provided that comprises a memory that stores computer executable components, and a processor that executes the computer executable components stored in the memory. The computer executable components can comprise a demand forecasting component that employs one or more first machine learning models to determine a total demand for tasks of a dynamic system within a defined time frame based on state information regarding a current state of the dynamic system, wherein the state information comprises task information regarding currently pending tasks of the tasks. The computer executable component can also comprise a turnaround time forecasting component that employs one or more second machine learning models to determine TATs for completing the tasks based on the state information, and a prioritization component that determines a prioritization order for performing the currently pending tasks based on the total demand and the TATs. In one or more embodiments in which the dynamic system comprises a medical care facility system, and the tasks include EVS tasks, the state information can include operating condition information regarding current operating conditions of the medical care facility system. In various embodiments, the prioritization component determines the prioritization order as a function of combinatorial optimization problem that minimizes the TATs.

In some implementations, the computer executable components can further comprise a data collection component that collects sets of historical state information for the dynamic system representative of historical performance of the tasks in association with different operating conditions of the dynamic system over sequential intervals of time. The computer executable components can also comprise a model development component that develops the one or more first machine learning models and the one or more second machine learning models based on the sets of historical state information. In one or more implementations, the model development component can continuously train and update the one or more first machine learning models and the one or more second machine learning models based on respective sets of the sets as they are collected over the sequential intervals of time.

In various embodiments, the computer executable components further comprise a resource allocation component that allocates available system resources to the tasks based on the total demand and the TATs. For example, the resource allocation component can allocate the available system resources to the tasks using an optimization function that minimizes the TATs. In some embodiments, the total demand reflects a total distribution of the tasks for performance within the defined time frame, including the currently pending tasks and forecasted tasks, and a total distribution of resources required for fulfilling the tasks within the defined time frame. With these embodiments, the computer executable components can further comprise a resources allocation component that allocates the available system resources to the tasks using an optimization function that minimizes an imbalance between the available system resources and the total distribution of resources required for fulfilling the tasks within the defined time frame.

The computer executable components can further comprise a resource assignment component that assigns respective resources of the available system resources to the tasks based on attributes associated with the respective resources that facilitate minimizing the TATs. For example, wherein the respective resources can include employees and the attributes include skill sets respectively associated with the employees. In this regard, the resource assignment component can assign employees to specific tasks based on their skill set in a manner that minimizes the TATs.

In some embodiments, the computer executable components can further comprise a system flow monitoring component that determines whether one or more of the TATs for one or more tasks of the tasks meets a defined TAT requirement for the one or more tasks. With these embodiments, the computer executable components can also comprise a notification component that generates a notification regarding failure of the one or more TATs to meet the defined TAT requirement based on a determination that the one or more TATs fail to meet the defined TAT requirement. The computer executable components can also comprise a resource monitoring component that determines whether the available system resources are sufficient to fulfill the tasks within the defined time frame based on the total demand. The notification component can also generate a notification regarding insufficient system resources based on determination that the available system resources required are insufficient to fulfill the tasks within the defined time frame.

In some embodiments, elements described in the disclosed systems can be embodied in different forms such as a computer-implemented method, a computer program product, or another form.

DETAILED DESCRIPTION

Figure 1:
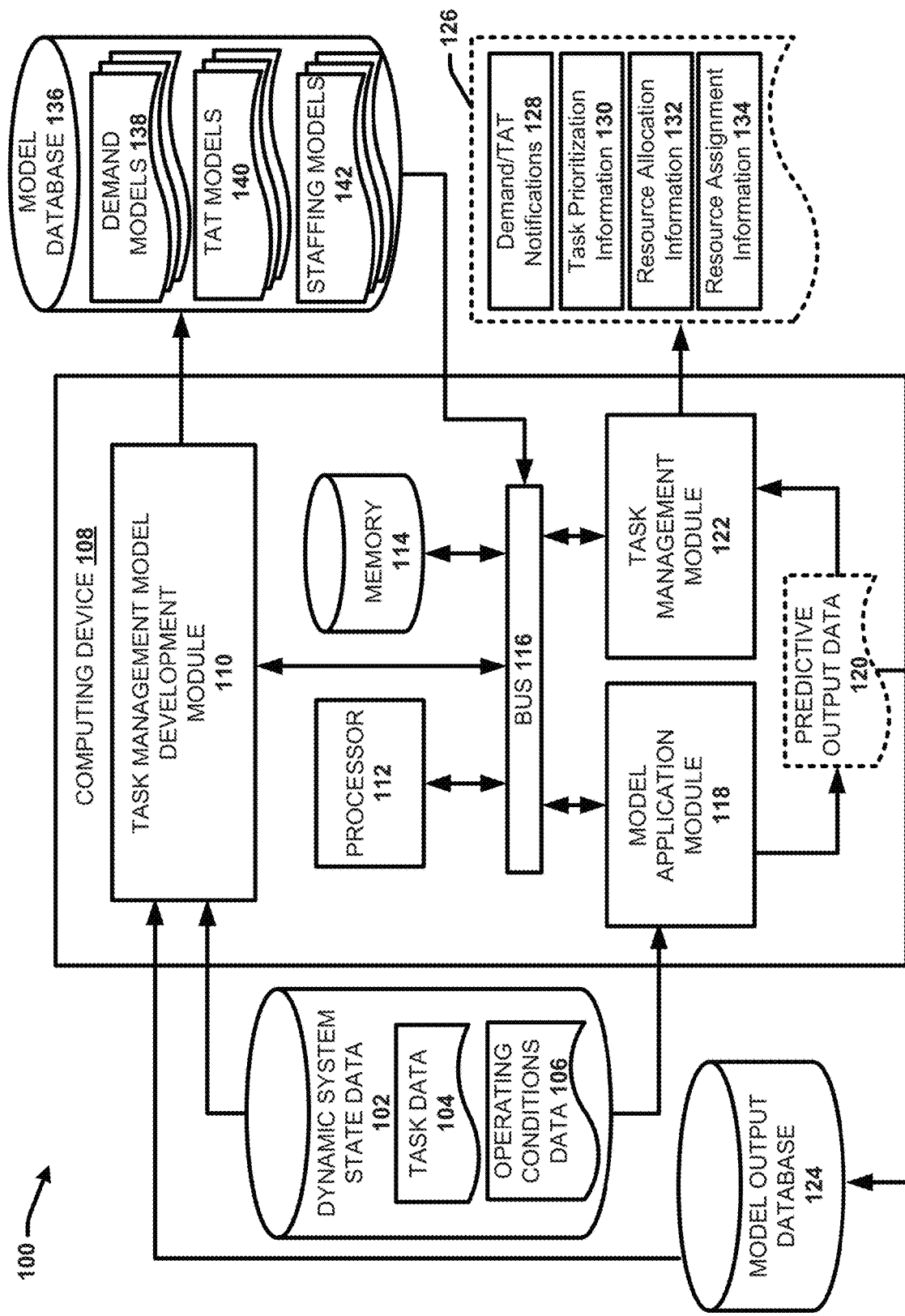
FIG. 1 illustrates a block diagram of an example, non-limiting system for managing tasks of a dynamic system with limited resources using a machine-learning and combinatorial optimization framework in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The disclosed subject matter is directed to systems, computer-implemented methods, apparatus and/or computer program products that provide for managing tasks of a dynamic system with limited resources using a machine-learning and combinatorial optimization framework. In various embodiments, the dynamic system is a medical care facility system (e.g., a hospital) and the disclosed systems, computer-implemented methods, apparatus and/or computer program products facilitate managing housekeeping services (also referred to as environmental services (EVS)) tasks of the medical care facility system to minimize turnaround times (TATs), (and subsequently reduce wait times for dirty beds) while fulfilling defined service requirements by combining diagnostic analytics, machine learning and combinatorial optimization.

Housekeeping services or EVS in the healthcare environment provide a key role in facilitating timely and quality patient care delivery. At high volume hospitals in which limited beds are available, the TAT for cleaning and preparing beds between patients can significantly impact patient placement and access to appropriate medical care, patient flow, and hospital capacity. To facilitate optimal patient flow throughout the hospital, EVS task managers need to manage operations by prioritizing the current housekeeping jobs and optimizing allocation of resources in view of the expected demand in the near future (e.g., the next 48 hours) and the estimated TAT for each housekeeping job. However, it is extremely difficult to estimate the demand for housekeeping resources and the TATs for different housekeeping jobs in a highly complex and dynamic hospital environment. In addition, there are often service level agreements (SLAs) set in place that define requirements for task TATs, cleaning effectiveness, availability and other system defined metrics that must be considered when managing performance and resource allocation for the EVS tasks.

One or more embodiments of the disclosed subject matter provide a system that facilitates managing and optimizing performance of EVS tasks of a hospital (or another type of dynamic medical care system) using a combination of adaptive learning and combinatorial optimization. The disclosed system combines machine learning with real-time and historical data regarding performance of EVS tasks under different operating conditions/contexts of the hospital to predict the demand for the EVS tasks within an upcoming time frame (e.g., the next hour, 12 hours, 24 hours, 48 hours, etc.), and to predict the TATs for the tasks. The system further employs machine learning and/or combinatorial optimization to determine how to prioritize/sequence the tasks and allocate available system resources to the tasks in real-time to minimize the TATs, meet the predicted demand, and meet defined SLAs for the tasks. By combing these techniques, the system can optimize EVS task prioritization and resource allocation based on the current state and forecasted state of the hospital while also accounting for the variability of dynamic hospital conditions and any SLAs for the tasks.

In this regard, the disclosed system can employ a microservices architecture to collect historical task data regarding EVS tasks performed and timing of performance (e.g., time task originated, and time fulfilled) in association with historical state information for the hospital regarding the various operating conditions/context of the hospital. For example, the state data can include information regarding occupancy levels, wait times for beds, status of beds, staff availability, supply availability, and the like. Using machine learning, the system learns complex relationships between hospital and EVS operating patterns and builds one or more machine learning models that can generate accurate predictions of the upcoming demand for different EVS tasks and the expected TATs of the tasks under based on current operating/contextual conditions of the hospital. For example, the system can analyze historical task data regarding amount, frequency and type of tasks performed or requested for performance in respective units of the hospital under different operating conditions/contexts of the hospital and build one or more machine learning models that can forecast the demand for EVS tasks in the respective units over an upcoming timeframe based on real-time data identifying a current operating/contextual state of the hospital. The system can also analyze relationships between the task TATs and factors affecting the TATs, such as job characteristics, current state of the hospital, demand for beds in respective units of the hospital, and the like, and build one or more machine learning models that can predict the TATs for various types of EVS jobs under various operation conditions and hospital states. The system can further periodically update the one or more task demand forecasting and/or TAT forecasting models based on newly collected data over time.

The system can further apply these machine learning models to forecast the demand for different EVS tasks over an upcoming timeframe (e.g., the next hour, 24 hours, etc.) and determine the estimated TATs for the EVS tasks, and employ combinatorial optimization and/or machine learning to determine how to prioritize/sequence the tasks and allocate available system resources to the tasks based on the forecasted demand and TATs. In this regard, the system can receive real-time task data regarding currently pending EVS tasks in association with real-time state data for the hospital (e.g., current occupancy levels, current status of beds, estimates of current wait times for beds, estimates of current wait times for beds, estimates of current demand for beds in respective units of the hospital, estimates of census pressure on source units where patients are waiting for a bed, current staff availability, etc.) and apply the one or more TAT forecasting models to predict the TATs for currently pending and predicted EVS tasks. The system can similarly apply employ the one or more demand forecasting models to predict the expected demand for EVS tasks over an upcoming timeframe based on the real-time task data and real-time state data. The system can further determine an optimal prioritization order/sequence for performing the tasks and/or an optimal allocation of the available system resources used for fulfilling the tasks (e.g., workers, supplies, etc.) to minimize the TATs, meet the predicted demand, and meet defined SLAs for the tasks. For example, the system can determine an optimal order/sequence for performing currently pending EVS tasks to minimize the TATs (and consequently reduce wait times) while meeting any defined operating constraints. The system can also employ combinatorial mathematical optimization to determine the number of resources to allocate to the respective units over the upcoming timeframe to minimize service level agreement (SLA) violations and maintain smooth patient flow based on the predicted task TATs and the expected demand.

The system can further provide recommendations regarding optimal task prioritization and resource allocation schemes to the EVS team (e.g., the manager, the individual workers, etc.) in real-time for implementation by the EVS team to facilitate EVS operations. In some implementations, the system can also evaluate the predicted task demand and the predicted task TATs in view of available system resources needed for fulfilling the tasks and/or SLAs defining any requirements for the tasks (e.g., requirements defining maximum allowed TATs for certain tasks, defining characteristics of resources allowed for competing certain tasks, etc.) to identify possible resource deficiencies and/or SLA violations. The system can further generate and provide the appropriate entities with notifications/alerts regarding potential deficiencies and/or SLA violations.

Various embodiments of the disclosed techniques are applied exemplified in association with management and optimization of EVS tasks of a hospital (or another medical care facility). However, the disclosed techniques can be applied to a variety of other types of dynamic systems to facilitate managing and prioritizing system tasks in which a limited/fixed amount of resources are available for performing the tasks, and in which the TATs and demand for the tasks are controlled by highly variable conditions/states of the system. For example, the disclosed techniques can be applied to facilitate managing/optimizing performance of housekeeping tasks of large hotel. In another example, the discloses techniques can be employed in wireless communication systems to facilitate managing scheduling and allocation of system resources (e.g., bandwidth, physical resource block assignments, layer partitioning, etc.) in association with dynamic network conditions. Thus, the disclosed techniques are not limited to a particular domain and be extended/applied to a variety of dynamic systems to manage a variety of different tasks.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates managing tasks of a dynamic system with limited resources using a machine-learning and combinatorial optimization framework in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. For example, in the embodiment shown, system 100 includes a computing device 108 that includes and a task management model development module 110, a model application module 118 and a task management module 122, which can respectively correspond to machine-executable components. System 100 also includes various electronic data sources and data structures comprising information that can be read by, used by and/or generated by the task management model development module 110, the model application module 118 and the task management module 122. For example, these data sources and/or data structures can include but are not limited to: a database comprising dynamic system state data 102, a model database 136 comprising one or more machine learning models (e.g., one or more demand models 138, one or more TAT models 140, and one or more staffing models 142), predictive output data 120, a model output database 124 and prescriptive output data 126.

The computing device 102 can include or be operatively coupled to at least one memory 114 and at least one processor 112. The at least one memory 114 can further store executable instructions (e.g., the task management model development module 110, the model application module 118 and the task management module 122) that when executed by the at least one processor 112, facilitate performance of operations defined by the executable instruction. In some embodiments, the memory 114 can also store one or more of the various data sources and/or structures of system 100 (e.g., the database comprising dynamic system state data 102, the model database 136, the predictive output data 120, the model output database 124 and/or the prescriptive output data 126). In other embodiments, one or more of the various data sources and structures of system 100 can be stored in other memory (e.g., at a remote device or system), that is accessible to the computing device 108 (e.g., via one or more networks). The computing device 108 can further include a device bus 116 that communicatively couples the various components and data sources of the computing device 108 (e.g., the task management model development module 110, the model application module 118 and the task management module 122, the processor 112, and the memory 114). Examples of said processor 112 and memory 114, as well as other suitable computer or computing-based elements, can be found with reference to FIG. 14, and can be used in connection with implementing one or more of the systems or components shown and described in connection with FIG. 1 or other figures disclosed herein.

In some implementations, the computing device 108, and/or the one or more of the various modules, components, and data sources/structure of system 100 (and other systems described herein) can be communicatively connected via one or more networks. In this regard, the one or more of the modules, components, and data sources/structure of system 100 (and other systems described herein) can be collocated and/or distrusted amongst different systems and/or devices/ machine and communicatively coupled via one or more networks. Such networks can include wired and wireless networks, including but not limited to, a cellular network, a wide area network (WAD, e.g., the Internet) or a local area network (LAN). For example, the computing device 108 can communicate with one or more system/devices of a medical care facility to access dynamic system state data 102 using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. The computing device 108 can thus include hardware (e.g., a central processing unit (CPU), a transceiver, a decoder), software (e.g., a set of threads, a set of processes, software in execution) or a combination of hardware and software that facilitates communicating information between the computing device 108 and externals systems, sources and devices.

In various embodiments, system 100 can facilitate managing/optimizing performance of tasks of a dynamic system (e.g., a hospital) using one or more machine learning models to forecast the expected demand for the tasks over an upcoming timeframe and the expected TATs for the respective tasks based a current state of the dynamic system. In the embodiment shown, the information regarding the current state of the dynamic system is provided by the dynamic system state data 102. In one or more embodiments, the dynamic system state data 102 comprises real-time data that reflects a current state of the dynamic system at a current point in time. As discussed in greater detail infra, the task management model development module 110 can collect and log sets of the dynamic system state data 102 over time to generate historical system state that can be used for developing and/or training the one or more machine models. System 100 can further employ machine learning and/or combinatorial optimization to determine how to prioritize/ sequence the tasks and allocate available resources of the dynamic system to the tasks in real-time to minimize the TATs, meet the predicted demand, and meet defined performance requirements for the tasks.

The various features and functionalities of system 100 can be dived into three components. The first component includes a model development component wherein the task management module development module 110 employs historical sets of the dynamic system state data 102 to develop and train one or more machine learning models (e.g., one or more demand models 138) to predict/forecast the demand for the system tasks in an upcoming time frame based on a current state of the dynamic system (e.g., determined using the dynamic system state data 102). The task management model development module 110 can also employ the historical sets of the dynamic system state data 102 to develop and train one or more machine learning models (e.g., one or more TAT models 140) to predict the TATs of the currently pending tasks (and optionally the forecasted tasks). The task management model development module 110 can also employ the historical sets of the dynamic system state data 102 to develop and train one or more machine learning models (e.g., one or more staffing models 142) to predict or estimate the number of staff that are or will be available to perform the tasks (e.g., the currently pending tasks and optionally the forecasted tasks).

The second component includes a model application component wherein the model application module 118 applies the one or more trained demand models 138, the one or more TAT models 140, and the one or more staffing models 142 to generate predictive output data 120 based on a current state of the system. In this regard, the predictive output data 120 can include the forecasted task demand (e.g., determined using the one or more demand model 138), the forecasted task TATs (e.g., determined using the one or more TAT models 140), and the predicted number of staff available to perform the tasks (e.g., determined using the one or more staffing models 142).

The third component includes the task management component wherein the task management module 122 employs the information regarding the forecasted task demand, the forecasted task TATs, and the forecasted staff available to facilitate determine how to prioritize/sequence the tasks and allocate available resources of the dynamic system to the tasks in real-time to minimize the TATs, meet the predicted demand, and meet defined SLA for the tasks.

In this regard, the dynamic system state data 102 can include task data 104 and operating conditions data 106. The task data 104 can include information regarding tasks of the dynamic system, including but not limited to: information identifying currently pending tasks, information regarding status of tasks being performed, information regarding timing of origination (e.g., when a request for the task was made), performance and completion of the tasks (e.g., that indicates task TAT), as well as various relevant attributes associated with the tasks. The attributes can vary based on the type of the dynamic system and the type of the tasks being managed. For example, in implementations in which the dynamic system is a hospital (or another type of medical care facility system), and the tasks include EVS jobs, the task data 104 can include information regarding known EVS jobs that need to be completed, including information identifying a type of the job (e.g., bed cleaning, bed cleaning for a specific type of bed, room cleaning, supply restocking, removal of waste, etc.), information identifying when the job originated, information identifying the status of the job (e.g., assigned, not begun, in process, etc.), information identifying who is assigned to the job if assigned, and information identifying or indicating attributes of the job. With respect to EVS jobs, the attributes can include but are not limited to: a location of the job (e.g., bed in room number 123 of hospital unit H needs cleaning), one or more characteristics/requirements of the EVS job (e.g., requirements of resources needed for the job, are required skill set or qualification of workers for performing the job), supplies needed for the job, a difficulty level of the job and the like. In some embodiments, different tasks or jobs can also be associated with attribute information that indicates a priority level of the task or job. For example, different type of EVS jobs can be associated with different priority levels that reflect the relative importance of the job (e.g., on a suitable scale, such as one or five wherein a classification of five indicates highest priority and a classification of one indicates lowest priority). For instance, an EVS job that involves the cleaning of a chemical spill of biohazardous material can be classified as a high priority job while an EVS job that involves cleaning the emergency room waiting area can be considered a lower priority job. The task data 104 can also include information regarding completed tasks, including information identifying the time completed or indicating the duration of time the task took to complete (e.g., the TAT), information identifying the resources used to complete the task (e.g., supplies, workers, etc.), performance metrics regarding the quality of performance of the task, and the like.

The operating conditions data 106 can include a variety of parameters regarding the operations conditions, context and or state of the dynamic system at a given point in time that can impact (e.g., either directly or indirectly) the demand for the system tasks (e.g., the amount/frequency/type of tasks expected over an upcoming defined period of time) and/or the TATs of the tasks. The operating conditions data 106 will also thus vary based on the type of dynamic system evaluated. For example, in implementations in which the dynamic system is a hospital and the tasks include EVS bed cleaning task, the operating conditions data 106 can include but is not limited to: current occupancy levels of the hospital, status of beds at the hospital (e.g., occupied, assigned, clean, dirty, etc.), number of patient waiting for beds, predicted wait times for occupied beds (e.g., determined based on level/type of care needed, recovery time, procedures scheduled, etc.), estimates of census pressure on source units where patients are waiting for beds, locations of the beds (e.g., by medical unit), and types of the beds. The operating conditions data 106 can also include staff data regarding the staff that perform the EVS tasks, as well as clinicians that provide the medical care (and thus influence patient flow), and other staff that perform a role at the hospital which influences patient flow directly or indirectly (e.g., equipment technicians, food service workers, etc.). For example, the staff data can include information regarding current staff activity (e.g., on job or break, specific jobs being completed by specific staff, number of staff members performing a specific task, etc.), staff availability, staff location, staff fatigue level, identities of the staff and the like. The operating conditions data 106 can also include information regarding supplies/equipment used in association with performance of the tasks, such as supply/equipment availability (e.g., available, in-use, out-of-stock), status (e.g., clean/dirty, etc.), supply/equipment location, and the like. The operating condition data 106 can include various additional types of information about the dynamic system that can or has been shown to historically effect (e.g., either directly or indirectly), task demand and/or task TAT. For example, in some implementations, the operating condition information can also include contextual information regarding time of day, day of week/year, weather, localized events or conditions at the hospital (e.g., emergency or crisis scenarios, disease outbreaks), local events associated high influx of patients, etc.), location and status of ambulatory services and the like.

With reference initially to the task management model development module 110, in one or more embodiments, the task management model development module 110 can train and develop of one or more machine learning models to determine the demand for certain tasks of a dynamic system within a defined, upcoming timeframe (e.g., from a current point in time through the next hour, the next 12 hours, the next 24 hours, the next 48 hours, etc.) based on historical system state data that reflects the demand for the tasks under different operating conditions. These one or more demand forecasting models are referred to herein and represented in system 100 as demand models 138. In various embodiments, the historical system state data can include past task data 104 and past operating conditions data 106 collected for the dynamic system over a past period of time. In this regard, in one or more embodiments, the task demand can be measured and/or represented by the distribution of tasks within the upcoming timeframe and can include currently pending tasks (known tasks to be completed) and forecasted tasks. For example, in implementations in which the dynamic system includes a hospital, the task management model development module 110 can train and develop one or more demand models 138 to predict the distribution of EVS tasks within an upcoming timeframe (e.g., from a current point in time through the next hour, the next 12 hours, the next 24 hours, the next 48 hours, etc.) based on historical information that reflects the historical demand for the EVS tasks (e.g., amount and type of that tasks performed and/or requested for performance) under different operating conditions/contexts of the hospital. For instance, the different operating conditions/contexts of the hospital can be based on variances in bed occupancy levels, bed availability, bed status, number of patients waiting for beds, type/location of the beds, staff availability, supply availability, and the like. The predicted distribution of the EVS tasks can include the total number of predicted tasks, the types of the tasks, the location of the tasks, and other potential distinguishing attributes associated with the tasks that can have an impact on the task TATs and/or the resources that are needed (e.g., personnel, supplies, equipment, etc.) to fulfil the tasks in accordance with defined service level requirements for the tasks.

In this regard, in a dynamic system such as a hospital, the predicted distribution of EVS tasks can be based on various complex and conditional factors. For example, the predicted distribution of EVS tasks involving bed cleaning can vary based on different operation conditions of the hospital regarding number of patients currently occupying beds, available clean beds, currently pending beds to be cleaned, number of patients waiting for beds, estimated wait times for the beds, locations of the beds, types of the beds, etc. and the predicted flow of the current patients and new patients throughout the hospital in the near future. By evaluating historical information regarding tasks performed or requested for performance under different operating conditions using one or more machine learning techniques, the task management development module 110 can learn complex correlations between how different operating condition and/or other contextual/state parameters (e.g., time of day, day of week/year, weather, events, etc.) influence the amount, frequency and/or type of tasks performed/needed. Based on these learned correlations, the task management model development module 110 can build and/or train the one or more demand models 138 to predict the demand for tasks within a defined, upcoming timeframe (e.g., over the next hour, over the next 12 hours, over the next 24 hours, etc.) based on the current operating conditions of the system. For example, with respect to a hospital system, the one or more demand models 138 can be configured to generate information that identifies the estimated total amount of EVS jobs in the next 24 hours. The one or more demand models 138 can also be configured to generate information that identifies the predicted distribution of the task as organized by one or more attributes of the tasks. For example, with respect to EVS tasks, the one or more demand models 128 can be configured to predict the amount of EVS jobs by type (e.g., bed cleaning, waste removal, etc.) and/or location (e.g., by hospital unit) needed over an upcoming defined period of time. For example, the one or more demand models 138 can be configured to determine an amount of anticipated bed cleaning tasks expected in the intensive care unit over the next 24 hours. In some embodiments, the one or more demand models 138 can be configured to generate demand information that forecasts the task demand over different periods of time into the future. For example, the one or more demand models 138 can be configured to generate demand information in incremental periods of time, such the expected EVS task amount/distribution for the next hour, for the next 6 hours, for the next 12 hours, for the next 24 hours and for the next 48 hours, based on a current state of the dynamic system. Once trained, the one or more demand models 138 can be stored in a model database 136 for subsequent retrieval and application by the model application modules 118.

The task management model development module 110 can also train and develop of one or more machine learning models to determine the expected TATs for the currently pending, and optionally the forecasted tasks, based on learned correlation between various factors in the historical dynamic system state data that influence the TATs. For example, the task management model development module 110 can learn correlations between TATs for different tasks (e.g. provided by historical task data 104 that indicates start and end times of the tasks), different operating conditions of the dynamic system (e.g., occupancy levels, wait times for occupied beds, staff availability, supply availability, etc.), and respective attributes associated with the different tasks (e.g., location, priority level, resource requirements, etc.). Based on these learned correlations, the task management development module 110 can develop and train one or more TAT models 140 to predict the TATs for currently pending tasks of the dynamic system give the current operating conditions/context of the system. For example, in implementations in which the dynamic system is a hospital (or another type of medical care facility), the TATs of different EVS jobs can vary based on job characteristics, job location, staff availability, current state of the hospital, demand for occupied or unclean beds in each medical unit, and the like. In this regard, using historical task information regarding the TATs of different tasks under the different operating conditions/contexts of the dynamic system, the task management model development module 110 can develop/train one or more TAT models 140 to predict the TATs of currently pending tasks and predicted tasks of the dynamic system. Once trained, the one or more TAT models 140 can also be stored in the model database 136 for subsequent retrieval and application by the model application modules 118.

The task management model development module 110 can also train and develop of one or more machine learning models to determine the expected number of staff available for performing the currently pending, and optionally the forecasted tasks, based on learned correlation between various factors in the historical dynamic system state data 102 that influence staff availability. For example, the task management development module 110 can train and develop one or more staffing models 142 to estimate the number of available staff (e.g., EVS workers) by shift or timeframe, by unit, or the like.

In various embodiments, the model development process can be an ongoing process that provides for continuously and/or regularly training and updating the one or more demand models 138 and/or the one or more TAT models 140 over time as new historical system state data is generated and received over the course of operation of the dynamic system. With these embodiments, the task management model development module 110 can regularly and/or continuously collect sequential sets of the dynamic system state data 102 (e.g., including task data 104 and operating conditions data 106) regarding the state, operating conditions and/or context of the dynamic system, the tasks that were performed and/or requested for performance in association with the different operating conditions and/or context of the dynamic system and the TAT of the tasks performed. For example, in implementations in which the system is a medical care facility (e.g., a hospital another type of medical care facility), the task management model development module 110 can collect sequential sets of such historical state information every N period of time (e.g., every 30 minutes, every hour, every 12 hours, every 24 hours, etc.). Each set of historical state information can thus provide a snapshot of the state of the dynamic system over time under different operating conditions/contexts and provide for identifying patterns/correspondences between different operating condition/context factors, task demand and TAT.

In this regard, as new historical data sets are received over time, the task management model development module 110 can train and update the machine learning models (e.g., the one or more demand models 138 and/or the one or more TAT models 140 predication models) on the new historical data sets. The training and updating can be continuously and/or regularly performed in accordance with a defined schedule (e.g., every N minutes, hours, or days, every X sequential data sets, etc.), or performed in a cyclic manner such that each time a model training and updating procedure is completed, a new model training and updated procedure can be initiated. In some implementations, the new historical data sets can be combined with previously collected data sets that were used to train a previous version of the one or more demand models 138 and/or the one or more TAT models 140. The combined (new and previously used for training) data sets can further be used to train each updated instance of the demand models 138 and/or TAT models 140. In other embodiments, the task management model development module 110 can cycle previously used data sets out of the current training data over time in accordance with a defined timeline.

Additional details regarding the training and development of the one or more demand models 138 and the one or more TAT models 140 by the task management model development module 110 are described infra with reference to FIGS. 3-6.

With reference now to the model application module 118, the model application module 118 can be configured to apply the one or more demand models 138, the one or more TAT models 140, and/or the one or more staffing models 142 to predict, based on a current state or operating context of the dynamic system represented by the dynamic system state data 102, one or more of the following: the demand for tasks of the dynamic system (e.g., total number to tasks, total number of tasks per medical unit, per type, or another grouping criteria), the TATs for the tasks, and the number of available staff to perform the tasks. For example, in implementations in which the dynamic system comprises a hospital (or another type of medical care facility), the model application module 118 can receive task data 104 that identifies the currently pending tasks (e.g., known task to be performed or completed) and attributes of the tasks (e.g., task type, task location, task characteristics/criteria etc.). The model application module 118 can also receive operating conditions data 106 that identifies current operating and contextual conditions of the dynamic system. For example, in implementations in which the dynamic system is a hospital, the current operating conditions/context information can include information regard current occupancy levels, current bed availably, current bed status (e.g., occupied, clean or dirty), number of patient waiting for beds, predicted wait times for occupied beds, estimates of census pressure on source units where patients are waiting for beds, locations of the beds (e.g., by medical unit), staff availability, supply/instrument availability, and the like. The current operating condition information can include various additional types of information about the dynamic system that can or has been shown to historically effect (e.g., either directly or indirectly), task demand, task TAT, and/or staff availability. For example, in some implementations, the operating condition information can also include contextual information regarding time of day, day of week/year, localized events or conditions at the hospital (e.g., emergency or crisis scenarios, disease outbreaks), local events associated high influx of patients, etc.) and the like.

Using the current task data and the current operating conditions data as input, the model application module 118 can further apply the one or more demand models 138 to generate demand information regarding the predicted distribution of tasks (e.g., number of tasks, types of the tasks, locations of the tasks, etc.) of the dynamic system from a current point in time over a defined period of time (e.g., the next hour, the next 12 hours, the next 24 hours, etc.). The model application module 118 can also apply the one or more TAT models to the current task data and the current operating conditions data to determine estimated TATs for the currently pending tasks and optionally the forecasted tasks. The model application module 118 can also apply the one or more staffing models 142 to the current task data and the current operating conditions data to determine the estimated number of staff available (e.g., per shift, per timeframe, per unit, etc.) to perform the currently pending tasks and optionally the forecasted tasks. In the embodiment shown, the forecasted demand, TAT, and staff availability information generated by the model application module 118 is collectively represented as predictive output data 120.

In one or more embodiments, the model application module 118 can be configured to apply the one more demand models 138, TAT models 140 and/or staffing models 142 in accordance with a defined schedule (e.g., every N minute, hours, etc.) to generate new/updated predictive output data 120 regarding predicted tasks, predicted TATs for the currently pending and the predicted tasks for the next defined period of time (or time periods), and the estimated number of available staff to perform the tasks. For example, with respect to a hospital system wherein the tasks managed include EVS tasks, based on current state information for the hospital (e.g., provided by the dynamic system stat data 102) the model application module 118 can generate predictive output data 120 that includes information regarding predicted demand for EVS tasks (e.g., total number of tasks needed for the next N hours, total number of tasks by hospital unit, by task type, etc. for the next N hours and the like), and predicted TATs for the currently pending tasks and optionally the predicted tasks. The predictive output data 120 can also include information regarding the estimated number of staff available to perform the tasks (e.g., per shift, per timeframe, per unit, etc.). The model application module 118 can further regenerate this predictive output data 120 every M minutes (e.g., every 30 minutes, every 60 minutes or another in accordance with another suitable time schedule) to account for changes in the state of the dynamic system over time. In this regard, each time the model application reapplies the one or more demand models, the one or more TAT models 140 and/or the one or more staffing models 142, the model application module 118 can receive updated system state data that reflect the current state of the system at the point in time. As a result, the predictive output data 120 can be regularly updated to reflect the current state of the dynamic system. In other embodiments, the model application module 118 can apply the demand, TAT and/or staffing forecasting models in response to request (e.g., by a system administrator, by an external system/entity, etc.). In some embodiments, the predictive output data 120 can be collected in a model output databased 124 and used by the task management model development module 110 to optimize the one or more demand models 138, the one or more TAT models 140 and/or the one or more staffing models 142 based on accuracy of the results as determined based on the actual task demand distribution, the actual task TAT and/or the actual staff available as subsequently observed in the dynamic system state data 102.

In various embodiments, the model application training and development process and the model application process are both ongoing and can occur simultaneously. In this regard, after an initial version of a demand model 138, TAT model 140 and/or staffing model 142 has been developed, the model application module 118 can receive current state information for the dynamic system regarding the current operating conditions/context of the dynamic system and apply the initial version of the demand or TAT model to the current state information to generate the predicted output data 120 regarding the forecasted demand for system tasks for an upcoming defined period of time (e.g., over the next hour, 12 hours, 24 hours, etc.) and/or the expected TATs of the tasks. At the same time, the task management model development module 110 can continue to collect sets of the dynamic system state data 102 and use the sets to train updated versions of the models. With these embodiments, each time model application is performed by the model application module 118 to predict the upcoming distribution of tasks over the next defined time period, the TATs for the currently pending and predicted tasks, and/or the staff available to perform the tasks, the model application module 118 can apply the most recently updated version of the corresponding model.

Figure 7:
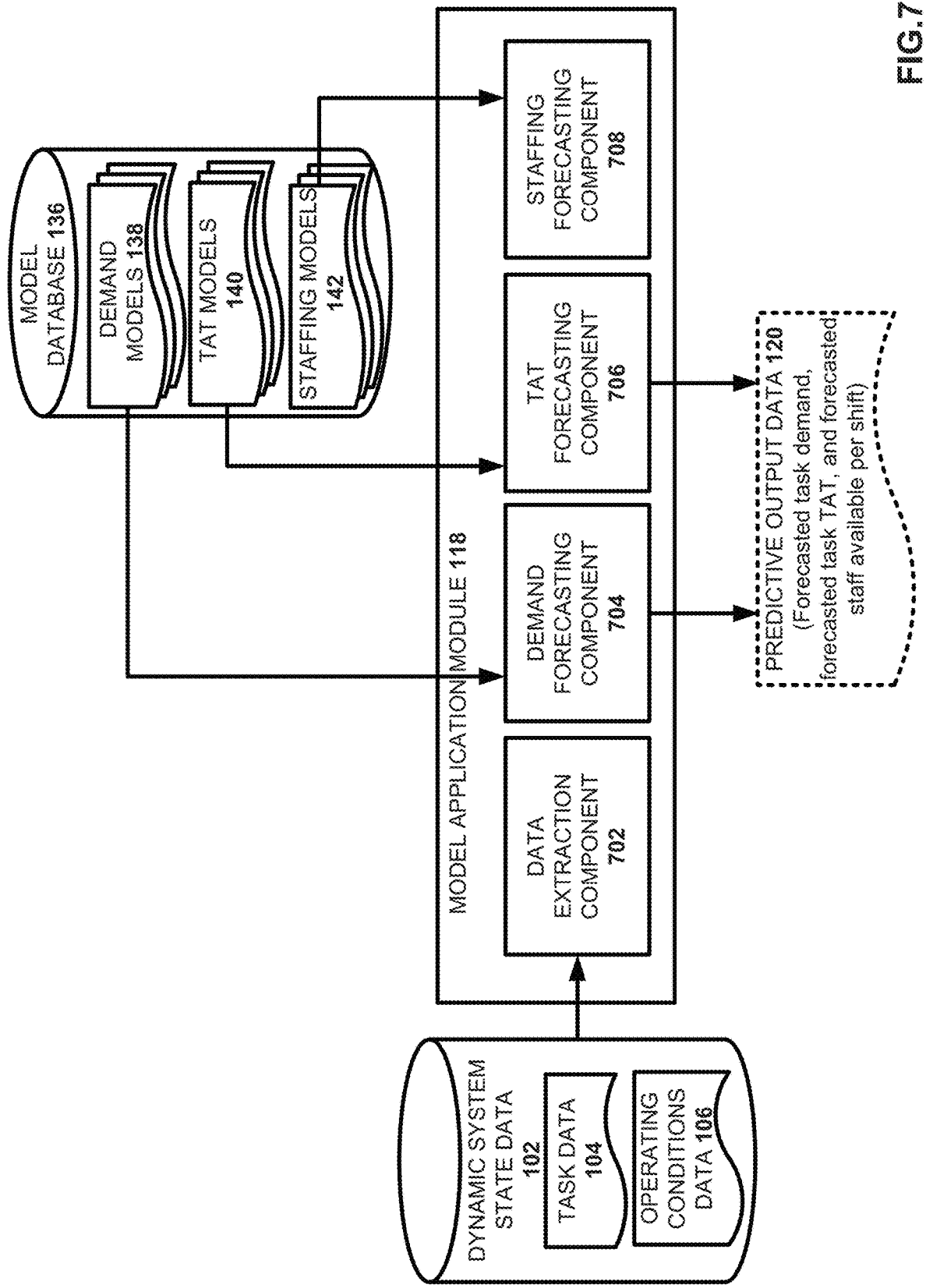
FIG. 7 presents an example model application module that applies one or more machine learning model to forecasting task TATs and system resource demands in real-time in accordance with one or more embodiments of the disclosed subject matter.

Additional details regarding the features and functionalities of the model application module 118 and the predictive output data 120 are described infra with reference to FIG. 7.

Referring now to the task management component, in one or more embodiments, the task management module 122 can utilize the predicted demand information, the predicted TAT information, and/or the predicted staff availability information (e.g., the predictive output data 120) to manage supply and demand, facilitate compliance with defined SLAs for the tasks, facilitate determining how to prioritize performance of the tasks, and optimizing allocation of available resources of the dynamic system for the tasks in real-time (e.g., in association with the current operating state of the dynamic system). For example, in some embodiments, the task management module 122 can evaluate the predicted demand for tasks over an upcoming timeframe in view of the resources of the dynamic system that are available for fulfilling the tasks to determine whether the available resources (e.g., workers, workers with specific qualifications/skill sets, supplies, equipment, etc.) are sufficient. The task management modules 122 can also determine whether the available resources are sufficient in view of any defined resource requirements/restrictions for the tasks. The task management module 122 can further generate a notification in real-time in scenarios in which the available resources are determined to insufficient to satisfy the forecasted demand and/or resources requirements/restrictions for forecasted tasks. In another embodiment, the task management module 122 can evaluate the predicted TATs for the currently pending tasks (and optionally the forecasted tasks) in view of defined performance requirements for one or more of the TATs to identify potential violations to the performance requirements. For example, the task management module 122 can determine whether the expected TAT for a specific task, and/the expected TATs for a group of tasks (e.g., grouped by type, grouped by hospital unit, or another suitable grouping criterion) exceeds a maximum allowed TAT defined to the task or group of tasks. The task management module 122 can further generate notifications regarding potential violations to the defined performance requirements for the TATs based on a determination that an expected TAT exceeds the maximum allowed TAT. In the embodiments shown, notifications regarding demand and TAT deficiencies/violations are represented as demand/TAT notifications 128. The task management module 122 can facilitate sending or otherwise providing a demand/TAT notification 128 to the appropriate entities in real-time in a suitable format (e.g., as a text message or email, as push notification that is displayed via a system monitor, as a notification posted in a communal forum, or the like).

The task management module 122 can also generate task prioritization information 130 that provides a prescriptive recommendation regarding how to prioritize and order the tasks determined at least in part based on the predictive output data 120. For example, the task management module 122 can employ combinatorial optimization to evaluate different prioritization schemes for the currently pending tasks based on the expected demand and the expected TATs for the pending tasks. The task management module 122 can further select an optimal prioritization scheme from the different prioritization schemes that facilitates minimizing the TATs, accounting for the expected demand and meeting defined SLA requirements for the tasks. The task management module 122 can then generate task prioritization information 130 that provides a recommendation regarding how to prioritize and order the tasks determined at least in part based on the predictive output data 120. The task management module 122 can also employ combinatorial optimization to determine resource allocation information 132 that defines an optimal allocation of the available resources for the tasks that facilitates minimizing the TATs, satisfying the expected demand, and meeting defined constraints/requirements for the tasks. In addition, in some embodiments, the task management module 122 can also determine resource assignment information 134 for the tasks that assigns specific resources, (e.g., specific works/staff, specific instruments/equipment, etc.) to specific tasks to facilitate minimizing the TATs, meeting defined SLAs, and ensuring the available resources will satisfy the expected demand With respect to assigning/allocating resources, the task management module 122 can further determine how to assign staff to tasks to maximize the number of tasks fulfilled while balancing staff workload (e.g., toward on equal distribution of the workload amongst the available staff) in view of the number of tasks to be completed and the number of staff available. The task management module 122 can also apply constraints regarding assignment restrictions, shift constraints (e.g., timing of shifts, maximum and minimum job allocation per staff member per shift, etc.) and capacity constraints (e.g., regarding system capacity) in association with task assignment rules (e.g., fair distribution of task rules, SLA rules, zone rules, patient and material transport rules, etc.) to determine how to optimize the assignment of staff members to the tasks (e.g. to optimize the number of tasks fulfilled and balance the distribution of the workload).

Figure 8:
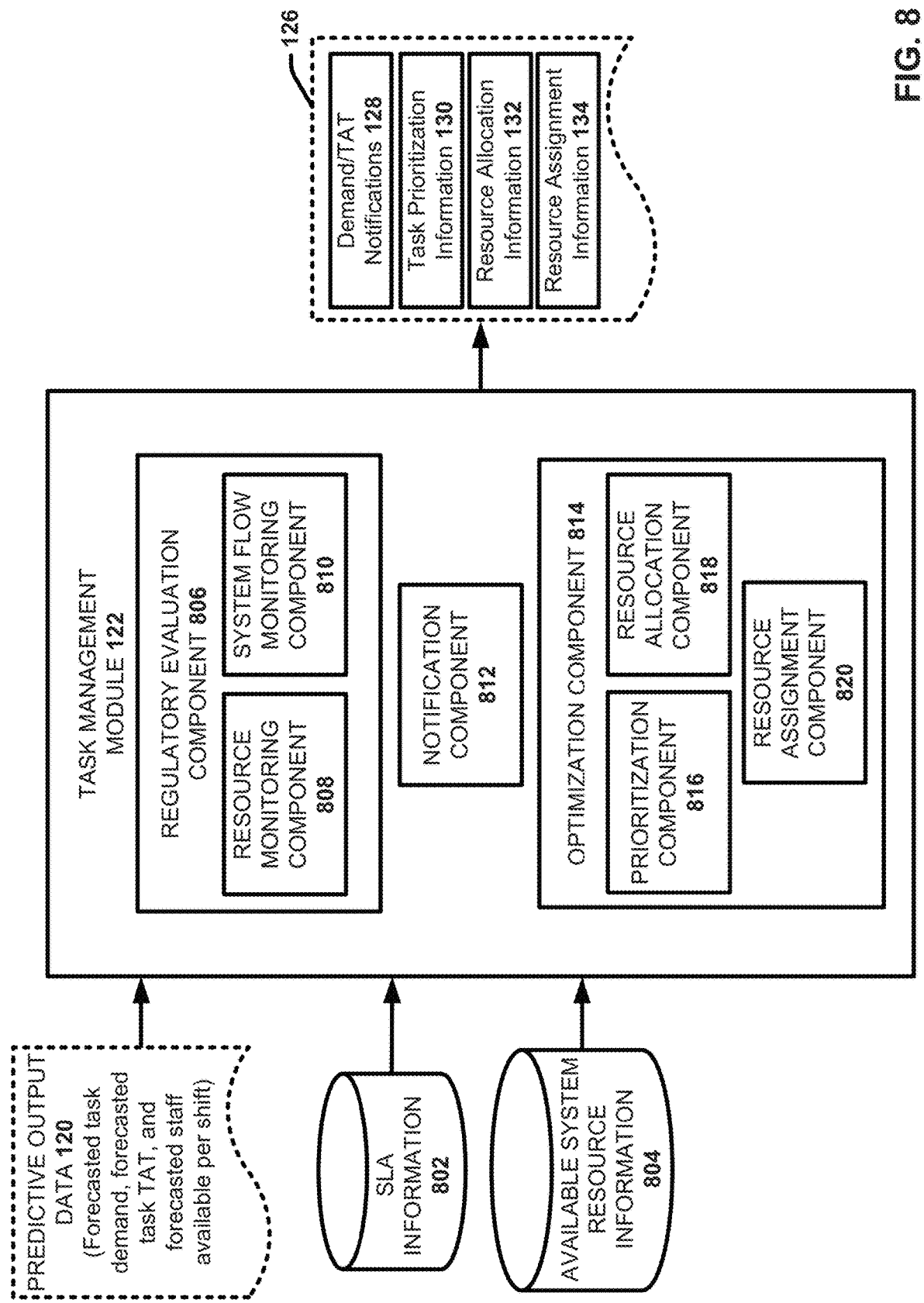
FIG. 8 presents an example task management module 122 that employs combinatorial optimization and/or machine learning techniques to manage tasks of a dynamic system based on task demand and/or task TAT in in accordance with one or more embodiments of the disclosed subject matter.

Additional details regarding the features and functionalities of the task management module 122 and the prescriptive output data 126 are described infra with reference to FIG. 8.

Figure 2:
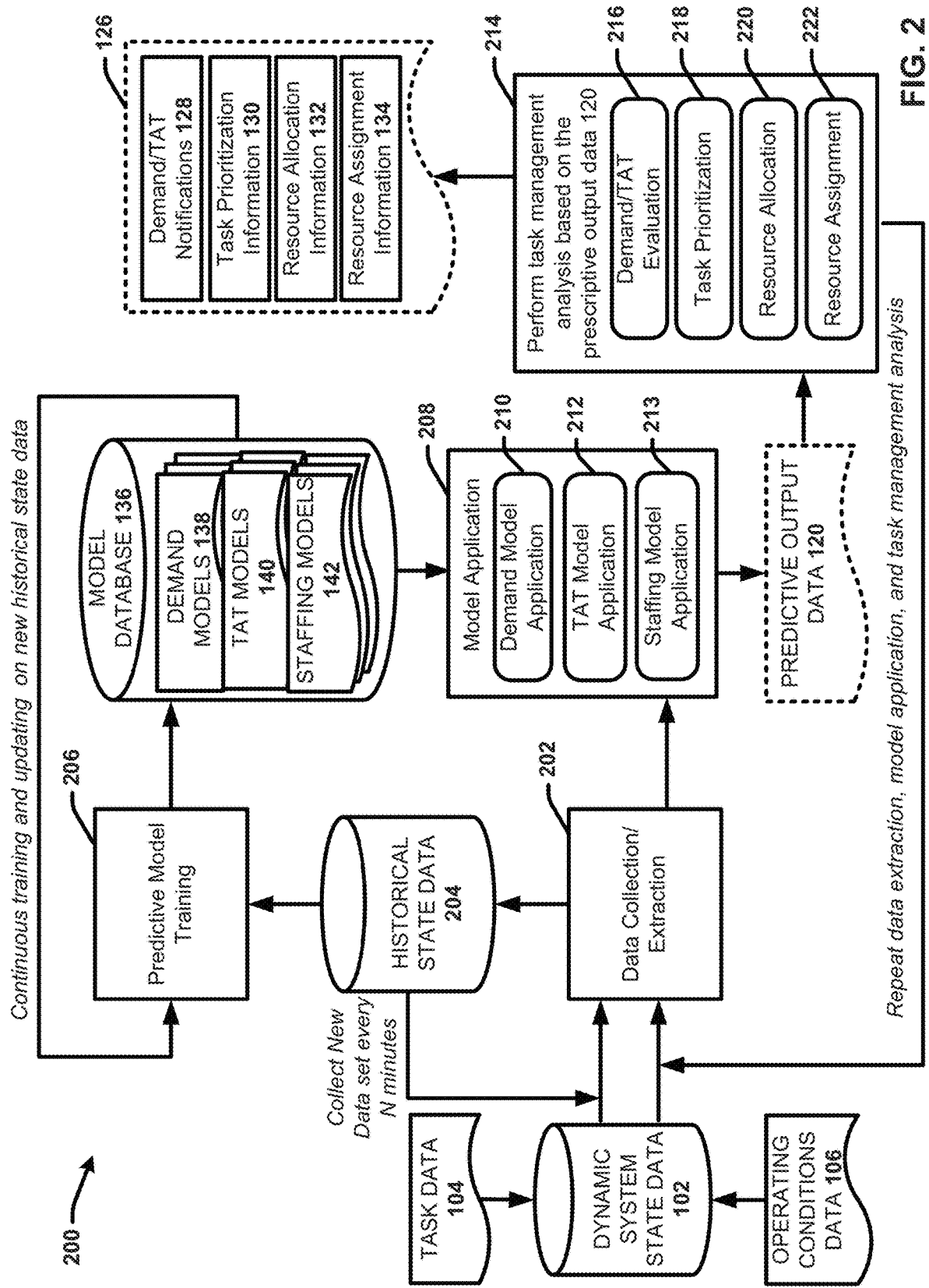
FIG. 2 illustrates a high-level flow diagram of an example process for managing tasks of a dynamic system with limited resources using a machine-learning and combinatorial optimization framework, in accordance with one or more embodiments of the disclosed subject matter.

FIG. 2 illustrates a high-level flow diagram of an example process 200 for managing tasks of a dynamic system with limited resources using a machine-learning and combinatorial optimization framework, in accordance with one or more embodiments of the disclosed subject matter. Process 200 combines the model development process of the task management model development module 110, the model application process of the model application module 118, and the task management process of the task management module 122 of system 100 in a unified fashion to facilitate managing performance of tasks of a dynamic system in real-time to optimize operations of the dynamic system. Repetitive description of like elements employed in respective embodiments is omitted for sake of brevity.

Process 200 begins at 202 wherein dynamic system state data 102 is collected or extracted for the purpose of model building/training and/or model application. In this regard, with respect to model building/training, at 202, the task management model development module 110 can regularly (e.g., every N minutes) collect and combine sets of the dynamic system state data 102 for the dynamic system over time to generate historical state data 204. The historical state data 204 can thus provide historical log of the task operations of the dynamic system under different operating conditions/context of the dynamic system. For example, in implementations in which the dynamic system comprises a hospital, at 202, the historical state data 204 can include sequential sets of task data 104 that identify the currently pending EVS tasks at sequential points or periods (e.g., periods of N minutes, such as 30 minutes for example) in time, information that indicates the TATs for tasks completed over the sequential period of time, and attributes of the tasks (e.g., types of the tasks, locations of the task, etc.). The historical state data 204 can also include sequential sets of operating conditions data 106 that coincide with the sequential sets of the task data 104 and that identify the operating conditions/contexts of the hospital at the sequential points or periods in time. In this regard, each set of the historical state data 204 can provide a snapshot of the state of the hospital at sequential points/periods of time.

At 206, the task management model development module 110 can employ the historical state data 204 to build and/or train the one or more demand models 138, the one or more TAT models 140, and/or the one or more staffing models 142. This historical data collection and model training can be a continuous process. In this regard, after initial versions of the one or more demand models 138, the one or more TAT models 140, and/or the one or more staffing models 142 are built, the task management model development module 110 can regularly or continuously collect sequential sets of the dynamic system state data 102 over time and add them to the historical state data 204. The task management model development module 110 can further regularly or continuously employ the updated historical state data 204 to retrain the one or more demand models 138, the one or more TAT models 140, and/or the one or more staffing models 142 to generate updated versions of the respective models.

With respect to the model application process, after initial versions of the one or more demand models 138, the one or more TAT models 140 and/or the one or more staffing models 142 have been developed, at 202 the model application module 118 can extract dynamic system state data 102 regarding the currently pending tasks of the dynamic system and/or tasks underway (e.g., represented by the tasks data 104), as well as current operating conditions data regarding current operating conditions of the dynamic system (e.g., represented by the operating conditions data 106). At 206, the model application module 118 can further apply the one or more demand models 138, the one or more TAT models 140 and/or the one or more staffing models 142 to the current representation of the dynamic system state data 102 to generate the predictive output data 120. For example, at 210 the model application module 118 can apply the one or more demand models 138 to the current representation of the dynamic system state data 102 to generate forested task demand data that identifies a total amount of tasks expected over the next M hours (e.g., the next hour, the next 12 hours, the next 24 hours, the next 48 hours, etc.), the total amount of tasks per type, the total amount of task per location (e.g., per hospital unit), the frequency of task requests expected over the next M hours, and the like. At 212, the model application module 118 can also apply the one or more TAT models 140 to the current representation of the dynamic system state data 102 to determine estimated TATs for the currently pending tasks (identified in the dynamic system state data 102), and in some implementations, the forecasted tasks (e.g., determined based on the demand model application 210). At 213, the model application module 118 can also apply the one or more staffing models 142 to the current representation of the dynamic system state data 102 to determine an estimated number/amount of staff members that are or will be available for performing for the currently pending tasks (identified in the dynamic system state data 102), and in some implementations, the forecasted tasks (e.g., determined based on the demand model application 210).

At 214, the task management module 122 can perform task management analysis based on the prescriptive output data 120. For example, at 216, the task management module 122 can determine whether the predicted demand and/or TATs indicate a shortage in available resources of the dynamic system and/or a potential violation to one or more SLA defined requirements. The task management module 122 can further generate demand/TAT notifications 128 based on a determination that a shortage or violation exists or is probable. In another example, at 216, the task management module 122 can determine an optimal prioritization order for performing the currently pending tasks that minimizes the TATs. The task management module 122 can further generate task prioritization information 130 regarding the optimal prioritization order. In another example, at 220, the task management module 122 can determine an optimal allocation of available system resources that facilitates meeting the expected demand, minimizing the TATs and/or meeting defined SLA requirements. The task management module 122 can further generate resource allocation information 132 regarding the optimal resource allocation scheme. In another example, at 222, the task management module 122 can determine how to assign specific resources (e.g., specific workers, supplies, etc.) to certain tasks in a manner that will result in minimizing the TATs, meeting defined SLA requirements, and accounting for the anticipated demand. For example, the task management module 122 can determine how to assign certain staff members to tasks in view of the estimated number of available staff members to perform the tasks to maximize the number of tasks fulfilled while balancing the distribution of the tasks assigned to equally amongst the available staff members. The task management module 122 can further generate resource assignment information 134 regarding the determined assignment of resources.

In various embodiment, the data extraction at 202 for the purpose of model application, the model application at 208, and task management analysis at 214 can be repeated over the course of operation of the dynamic system to generate up to date prescriptive output information 126 that reflects the current operating state/condition of the dynamic system. For example, in implementations in which the dynamic system is a hospital, the data extraction, model application, and task management analysis can be repeated every 30 minutes or every hour.

Figure 3:
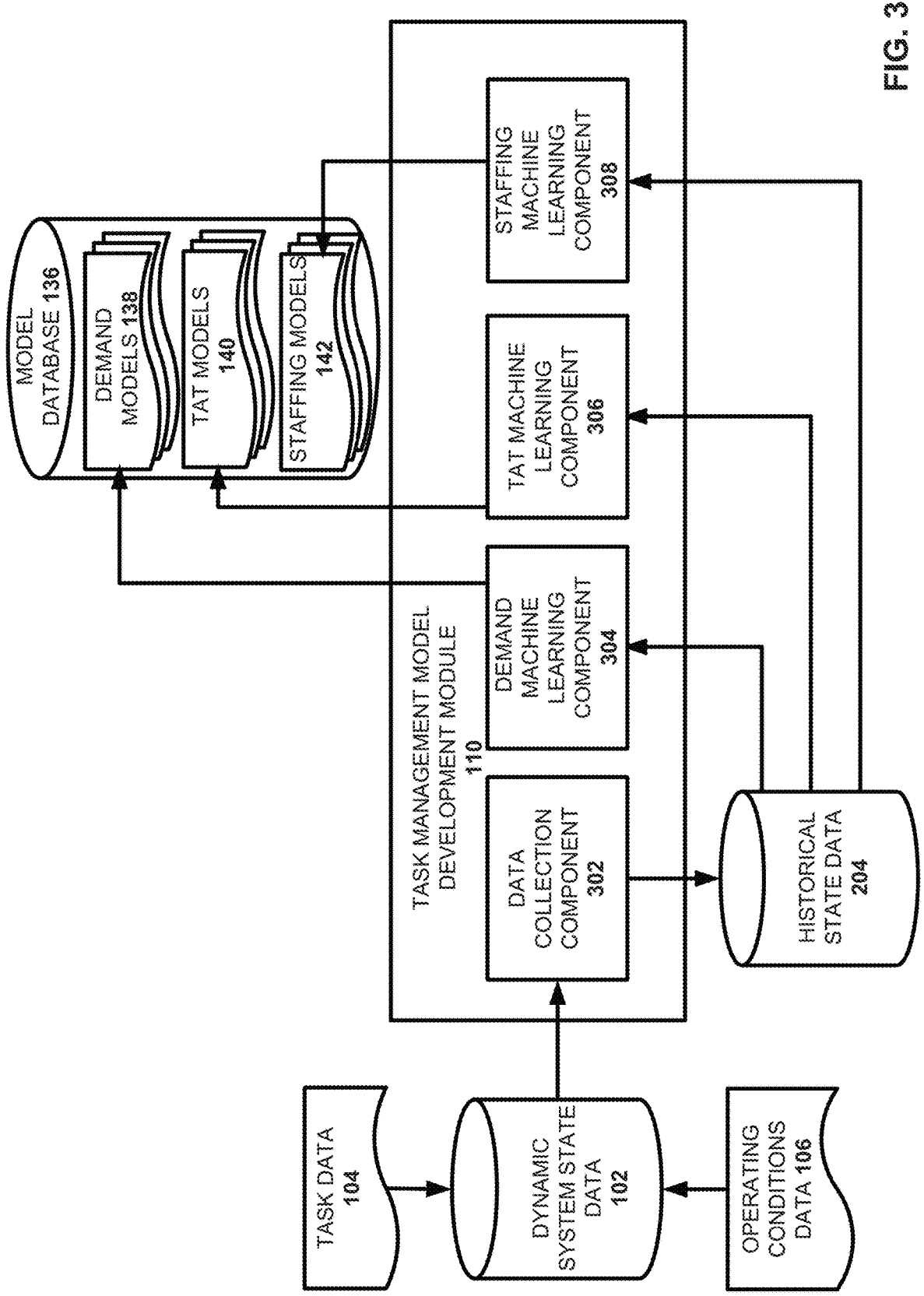
FIG. 3 presents an example task management model development module that develops machine learning models for forecasting task TATs and system resource demands in accordance with one or more embodiments of the disclosed subject matter.

FIG. 3 presents an example task management model development module 110 that develops machine learning models for forecasting task TATs and system resource demands in accordance with one or more embodiments of the disclosed subject matter. Repetitive description of like elements employed in respective embodiments is omitted for sake of brevity.

In one or more embodiments, the task management model development module 110 can include a data collection component 302, a demand machine learning component 304, a TAT machine learning component 306 and a staffing machine learning component 308. The data collection component 302 can be configured to collect sets of the dynamic system state data 102 over time as it is generated in association with operation of the dynamic system to generate the historical state data 204. The demand machine learning component 304 can be configured to train and develop the one or more demand models 138 based on the historical state data 204. The TAT machine learning component 306 can be configured to train and develop the one or more TAT models 140 based on the historical state data 204. The staffing machine learning component 308 can be configured to train and develop the one or more staffing machine learning models 142 based on the historical state data 204.

In various implementations in which the dynamic system is a hospital (or another medical care system), the one or more demand models 138 can be configured to estimate the demand for tasks of the dynamic system over an upcoming period of time, such the next hour, the next 12 hours, the next 24 hours, the next 48 hours, etc. The demand for task can include information that identifies or indicates the total number of tasks needed for performance over the defined period of time. In this regard, the estimated demand can identify the currently pending tasks that are currently requested and have not yet been completed, as well as the forecasted tasks that are expected to arise over the defined period of time.

In some embodiments, the one or more demand models 138 can include one or more models that are configured to estimate demand over different periods of time. For example, the one or more demand models 138 can include a first model that estimates the demand over the next hour, a second model that estimates the demand over the next 2 hours, a third model that estimates the demand over the next 3 hours, a fourth model that estimates the demand over the next 6 hours, a fifth model that estimates the demand over the next 12 hours, a sixth model that estimates the demand over the next 24 hours, and so on. According to these embodiments, in implementations in which the dynamic system is a hospital and the tasks include EVS tasks, the one or more demand models 138 can be configured to generate demand estimation information that identifies or indicates the total amount of EVS task needed for performance over the next hour, over the next two hours, over the next three hours, over the next 24 hours, over the next 48 hours, etc. In other embodiments, the one or more demand models 138 can include one or more models that can further determine demand on an attribute level. For example, the one or more demand models 138 can include one or more models be configured to determine demand by task type (e.g., number of bed cleaning tasks in the next N hours), by task location (e.g., number of bed cleaning tasks in hospital unit B in the next N hours), by task priority level (e.g., number of EVS task classified as high priority in the next N hours), or another distinguishable attribute.

The one or more TAT models 140 can be configured to estimate the expected TATs of different tasks based on a current operating scenario/state of the dynamic system. For example, the one or more TAT models 140 can be configured to generate TAT information that indicates the estimated TATs of the currently pending (e.g., unfulfilled or in progress) tasks. The one or more TAT models 140 can also include one or more models that can estimate the expected TATs of the forecasted tasks. For example, assuming the one or more demand models 138 generate information that estimates there will be 50 additional (in addition to the currently pending tasks) bed cleaning tasks in hospital unit C over the next 12 hours. The one or more TAT models 140 can include one or more models that can also generate information regarding the expected TATs of those 50 bed cleaning tasks. For example, the one or more TAT models 140 can generate information that indicates the average TATs of each of the 50 bed cleaning tasks will be 10 minutes. In some embodiments, the one or more TAT models 140 can include one or more models that are configured to generate TATs for tasks on an attribute level. For example, the one or more TAT models 140 can include TAT models configured to estimate TATs for tasks by type (e.g. expected TATs for bed cleaning tasks, expected TATs for waste removal tasks, etc.), by location (e.g., expected TATs of tasks in hospital unit A, expected TATs of tasks in hospital unit B, etc.), by priority level (e.g., expected TATs of high priority tasks, expected TATs of low priority tasks, etc.), or another distinguishable attribute.

The one or more staffing models 142 can be configured to estimate the expected number/amount of staff available to perform the currently pending and/or estimated tasks based on a current operating scenario/state of the dynamic system. For instance, the one or more staffing models 142 can be configured to generate staff availability information that indicates the estimated number of staff members available for performing tasks per defined time frames (e.g., shifts), per unit, or the like. For example, the staffing machine learning component 308 can evaluate the current state of the system, including current scheduling information, current staff assignments, current staff locations, current staff activities and the like, to predict the distribution of staff available to perform tasks in an upcoming time frame, in a particular unit, or the like. In accordance with this example, the staffing models 142 can include a model that estimates the number of staff members that will be available to perform tasks over the next hour, over the next 6 hours, over the next 24 hours, and the like.

In some embodiments, the demand machine learning component 304, the TAT machine learning component 306, and/or the staffing machine learning component 308 can respectively be configured to employ and combine various different types of machine learning techniques for the demand models 138, the TAT models 140 and/or the staffing models. In this regard, various different types of machine learning algorithms/models exist or are being added to the AI field that have different strengths and weakness. For example, some suitable machine learning algorithms/models that can be used for the one or more demand models 138, the one or more TAT models 140, and/or the one or more staffing models can include but are not limited to: a nearest neighbor algorithm, a naïve Bayes algorithm, a decision tree algorithm, a boosting algorithm, a gradient boosting algorithm, a linear regression algorithm, a neural network algorithm, a k-means clustering algorithm, an association rules algorithm, a q-learning algorithm, a temporal difference algorithm, a deep adversarial network algorithm, or a combination thereof. Some of theses models may be more conservative than another in association with forecasting task demand or TAT based on application of the historical state data 204.

Thus, in some embodiments, the demand machine learning component 304 can simultaneously develop and train different types of machine learning models to generate demand estimates based on the historical state data 204, wherein the different types of machine learning models employ different types of machine learning algorithms/techniques (e.g., a k-means clustering vs. a deep convolutional neural network algorithm). With these embodiments, each of the different models can respectively generate different output predictions regarding the expected demand. The demand machine learning component 304 can further combine/fuse the different output predictions in accordance with a defined weighting scheme to generate a final output prediction that balances the strengths and weaknesses of the different types of machine learning models. With theses embodiments, the demand models 138 can include a plurality of different types of machine learning models configured to estimate the task demand for an upcoming period of time using a different type of machine learning algorithm.

Figure 4:
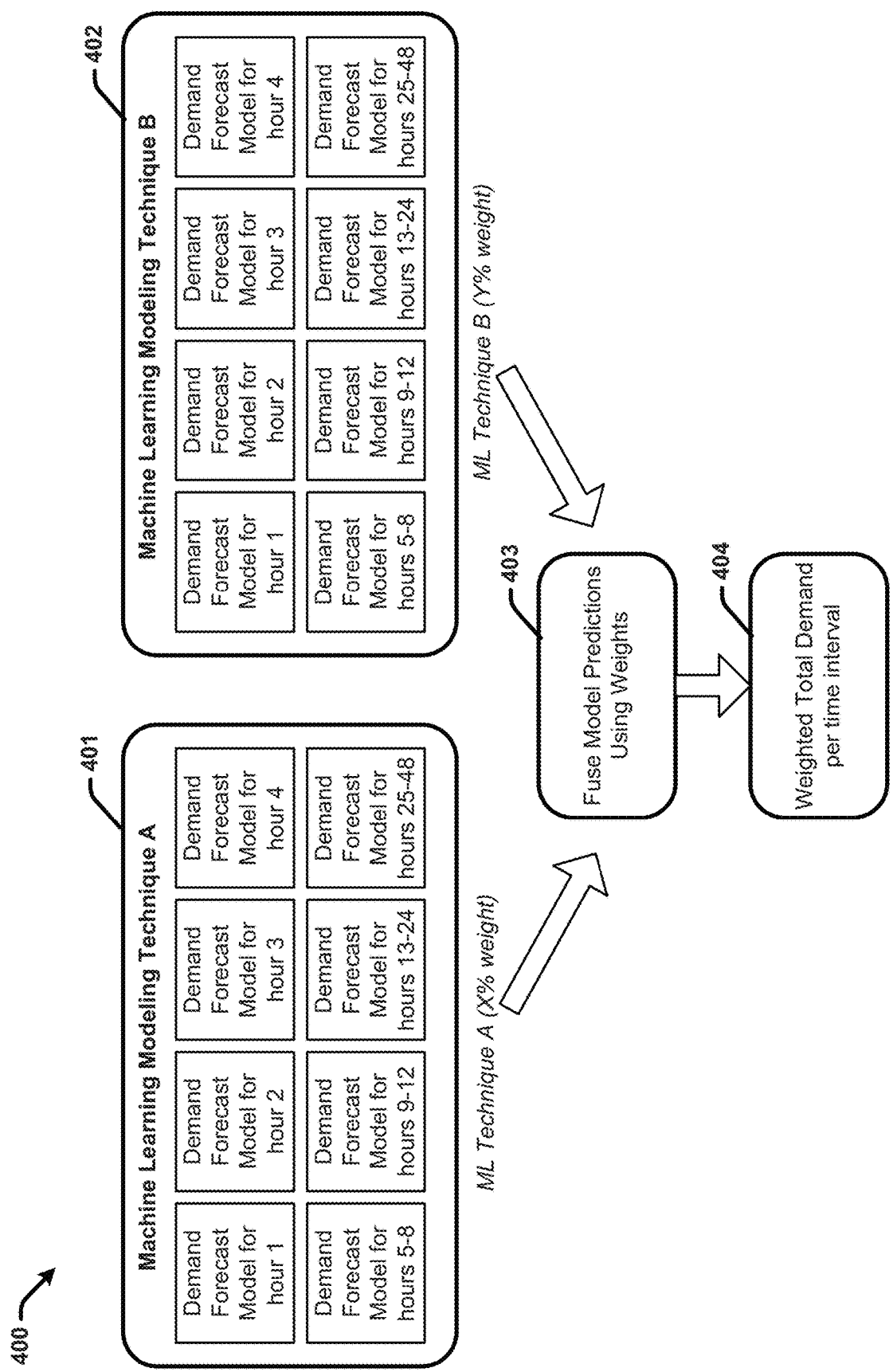
FIG. 4 presents an example flow diagram of an example process for developing machine learning models for forecasting task TATs and system resource demands in accordance with one or more embodiments of the disclosed subject matter.

For example, FIG. 4 presents an illustration of an example model fusion technique 400 for combining different types of machine learning models to forecast system resource demands in accordance with one or more embodiments of the disclosed subject matter. In the embodiment shown, the demand machine learning component 304 can develop and train a first set 401 of demand models using a first machine learning technique, referred to as machine learning modeling technique A. The demand machine learning component 304 can also develop and train a second set 402 of demand models using a second machine learning modeling technique, referred to as machine learning technique B. For example, the machine learning modeling technique A can include a gradient bosting machine learning technique while the machine learning modeling technique B can include a deep neural machine learning technique. Each set of demand models includes a separate model that is tailored to estimate the demand for a different upcoming timeframe. For example, each set of machine learning models includes a separate demand forecasting model for hour 1, hour 2, hour 3, hour 4, hours 5-8, hours 9-12, hours 13-24 and hours 25-48. In this regard, the demand machine learning component 304 can not only develop and train different types of machine learning models to generate demand estimates using different machine learning algorithms, but different models configured to estimate the demand for different future periods of time, based on a current state of the dynamic system. Thus, the output of the first set 401 of machine learning models will include eight demand estimates estimated using machine learning modeling technique A, one for each designated timeframe. Likewise, the output of the second set 402 of machine learning models will include eight demand estimates estimated using machine learning modeling technique B, one for each designated timeframe. It should be appreciated that the number of models included in each set and the specific timeframes associated with the respective models is merely exemplary and can vary.

The demand machine learning component 304 can further weigh the respective demand estimates of the first set 401 of demand models and the second set of demand models 402 using a predetermined weighting scheme that accounts for the strengths and weaknesses of the respective machine learning modeling techniques. For example, in the embodiment shown, the machine learning technique A estimates can be given a weight of X % while the machine learning technique B estimates can be given a weight of Y %. At 403, the demand machine learning component 304 can fuse the model predictions using the predefined weights to generate a final, weighted estimate of the total demand per time interval at 404.

With reference again to FIG. 3, the TAT machine learning component 306 can similarly simultaneously develop and train different types of machine learning models to generate TAT estimates based on the historical state data 204, wherein the different types of machine learning models employ different types of machine learning algorithms/techniques (e.g., a k-means clustering vs. a deep convolutional neural network algorithm). With these embodiments, each of the different models can respectively generate different output predictions regarding the expected TAT. The TAT machine learning component 306 can further combine/fuse the different output predictions in accordance with a defined weighting scheme to generate a final output prediction that balances the strengths and weaknesses of the different types of machine learning models. With these embodiments, the TAT models 140 can include a plurality of different types of machine learning models configured to estimate the TAT for respective tasks or groups of tasks (e.g., grouped in accordance with a common attribute) using a different type of machine learning algorithm.

Figure 5:
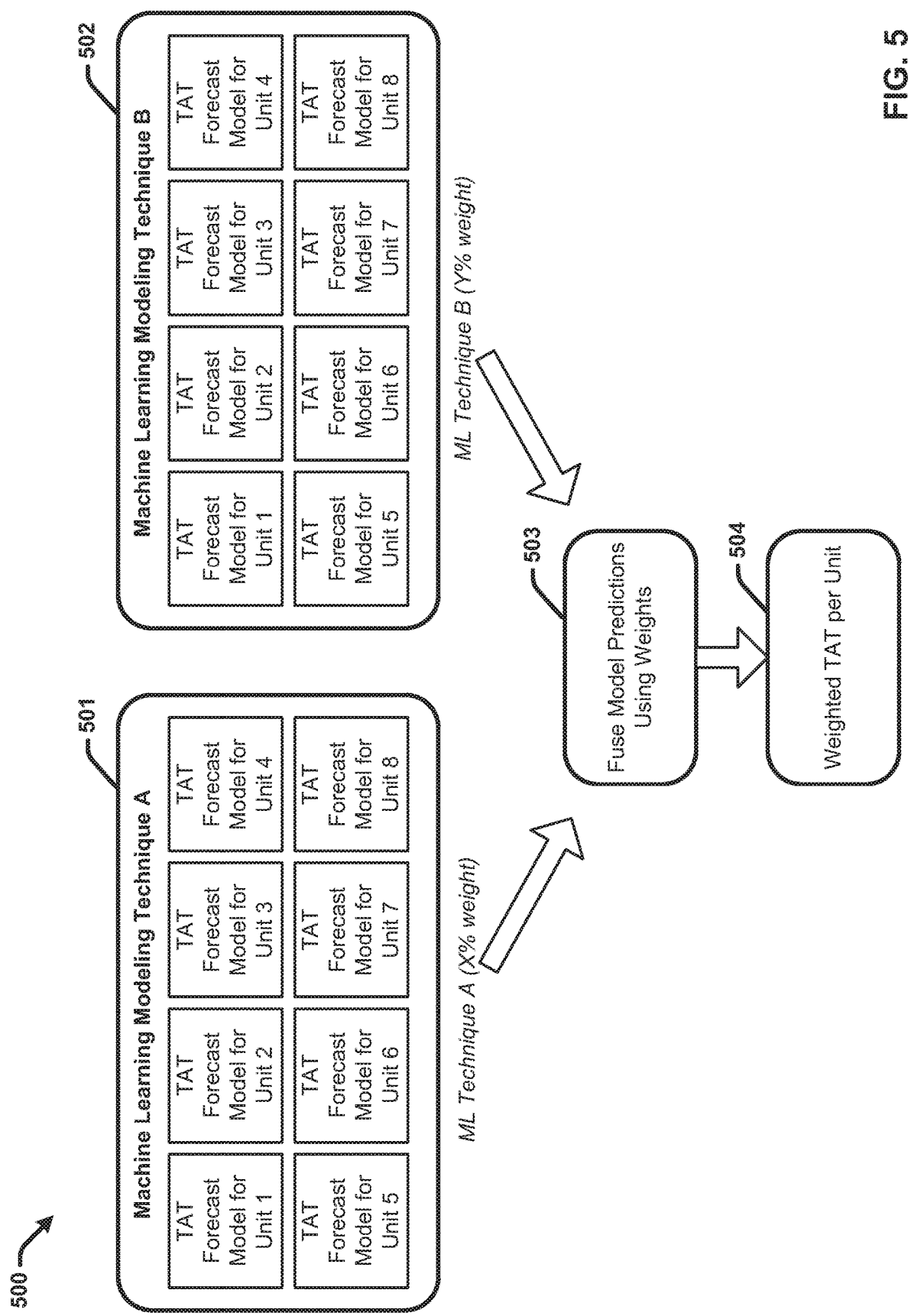
FIG. 5 presents an illustration of an example model fusion technique for combining different types of machine learning models to forecast system resource demands in accordance with one or more embodiments of the disclosed subject matter.

For example, FIG. 5 presents an illustration of an example model fusion technique 500 for combining different types of machine learning models to forecast task TATs in accordance with one or more embodiments of the disclosed subject matter. In the embodiment shown, the TAT machine learning component 306 can develop and train a first set 501 of TAT forecasting models using a first machine learning technique, referred to as machine learning modeling technique A. The TAT machine learning component 306 can also develop and train a second set 502 of TAT forecasting models using a second machine learning modeling technique, referred to as machine learning technique B. For example, the machine learning modeling technique A can include a gradient bosting machine learning technique while the machine learning modeling technique B can include a deep neural machine learning technique. Each set of TAT forecasting models further includes a separate model that is tailored to estimate the TATs for the pending (and/or forecasted) tasks in a different unit of a hospital (e.g., assuming the dynamic system in this example is a hospital). For example, each set of machine learning models includes a separate TAT forecasting model for unit 1, unit 2, unit 3, unit 4, unit 5, unit 6, unit 7 and unit 8. In this regard, the TAT machine learning component 306 can not only develop and train different types of machine learning models to generate TAT estimates using different machine learning algorithms, but different models configured to estimate the TATs for tasks associated with different units, based on a current state of the hospital. Thus, the output of the first set 501 of machine learning models will include eight TAT estimates regarding the average TATs for tasks in the corresponding unit, estimated using machine learning modeling technique A. Likewise, the output of the second set 502 of machine learning models will include eight demand estimates regarding the average TATs for tasks in the corresponding unit, estimated using machine learning modeling technique B. It should be appreciated that the number of models included in each set and the specific attribute associated with the respective models is merely exemplary and can vary. For example, in other embodiments, different models included in set can be tailored to determine TAT by task type, by task priority level, or another suitable attribute.

The TAT machine learning component 306 can further weigh the respective TAT estimates of the first set 501 of TAT models and the second set of TAT models 502 using a predetermined weighting scheme that accounts for the strengths and weaknesses of the respective machine learning modeling techniques. For example, in the embodiment shown, the machine learning technique A estimates can be given a weight of X % while the machine learning technique B estimates can be given a weight of Y %. At 503, the TAT machine learning component 306 can fuse the model predictions using the predefined weights to generate a final, weighted estimate of the average task TAT per time per unit 504.

Figure 6:
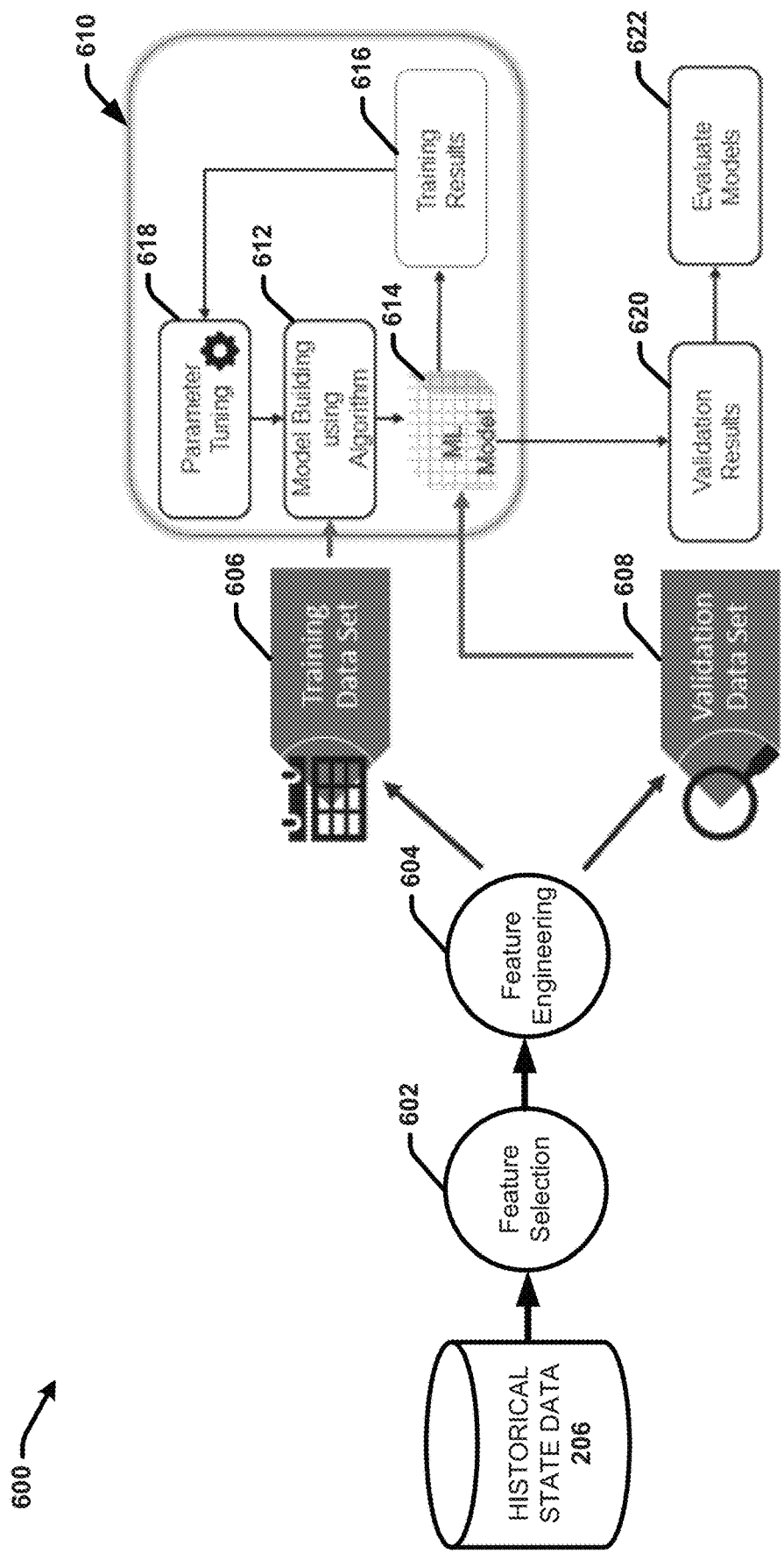
FIG. 6 presents an illustration of an example model fusion technique for combining different types of machine learning models to forecast task TATs in accordance with one or more embodiments of the disclosed subject matter.

FIG. 6 presents an example flow diagram of an example process 600 for developing machine learning models for forecasting task TATs and system resource demands in accordance with one or more embodiments of the disclosed subject matter. In various embodiments, the demand machine learning component 304 can apply process 600 to develop and train the one or more demand models 138, and the TAT machine learning component 306 can apply process 600 to develop and train the one or more TAT models 140. Repetitive description of like elements employed in respective embodiments is omitted for sake of brevity.

In this regard, with reference to FIG. 6 in view of FIG. 3, the machine learning model training and development process 600 applied by the demand machine learning component 304 and/or the TAT machine learning component 306 can initially involve features selection 602 and feature engineering 604. The feature selection 602 involves selecting features from the historical state data 204 that are determined to have an impact on task demand and/or task TAT. The specific features that are selected are respectively determined by the demand machine learning component 304 and the TAT machine learning component 306 based on learning patterns/correlations between the respective features in the historical state data 204 and task demand and task TAT, respectively. The feature engineering 604 involves determining the relative importance/impact of the selected features on task demand and/or TAT, (depending on the model being developed/trained) based on further analysis of patterns/correlations in the historical state data 204. In this regard, in implementations in which process 600 is employed to develop/train one or more demand models 138, the demand machine learning component 304 can determine weights and/or coefficients for the selected features that reflects their relative impact on task demand based on analysis of the historical state data 204. Likewise, in implementations in which process 600 is employed to develop/train one or more TAT models, the TAT machine learning component 306 can determine weights and/or coefficients for the selected features that reflects their relative impact on task TAT based on analysis of the historical state data 204.

The extracted/selected features are further divided into a training data set 606 and a validation data set 608. The training data set 606 is used to train and build the machine learning model 414 in accordance with process 610. In this regard, the machine learning model 414 can be or correspond to a demand model of the one or more demand models 138 or a TAT model of the one or more TAT models. Process 410 involves model building at 612 using one or more machine learning algorithms, generating and evaluating the training results 616, and parameter tuning 618. The type of the machine learning algorithm can vary. For example, the machine learning algorithm can include but is not limited to, a nearest neighbor algorithm, a naïve Bayes algorithm, a decision tree algorithm, a linear regression algorithm, a neural network algorithm, a k-means clustering algorithm, an association rules algorithm, a q-learning algorithm, a temporal difference algorithm, a deep adversarial network algorithm, or a combination thereof. In some embodiments, as described above, infra with reference to FIGS. 4 and 5, a plurality of different types of machine learning algorithms can be used to generate different types of demand models 138 and/or TAT models 140 with different strengths and weaknesses. These different types of machine learning models can be used to generate different task demand and/or TAT predictions which can be combined to generate a final predication of task demand and/or TAT that balances the strengths and weaknesses of the different models.

Once the machine learning model 614 is built, the validation data set 608 can be applied to the model to generate validation results 620 which can be evaluated at 622 to evaluate the performance accuracy and specificity of the model. Process 600 can be repeated on a regular basis (e.g., every 12 hours, every 24 hours, etc.) to fine tune and update the one or more demand models 138 and/or the one or more TAT models 140 based on newly collected historical state data 204 collected over the operation of the dynamic system (e.g., by the data collection component 302).

FIG. 7 presents an example model application module 118 that applies one or more machine learning model to forecasting task TATs and system resource demands in real-time in accordance with one or more embodiments of the disclosed subject matter. In the embodiment shown, the model application module 118 can include data extraction component 702, demand forecasting component 704, TAT forecasting component 706, and staffing forecasting component 708. Repetitive description of like elements employed in respective embodiments is omitted for sake of brevity.

The model application module 118 can be configured to apply the one or more demand models 138, the one or more TAT models 140, and/or the one or more staffing models 142 during operation of the dynamic system (in real-time) to generate the predictive output data 120. In this regard, after initial versions of the one or more demand models 138, the one or more TAT models 140, and/or the one or more staffing models 142 have been developed and trained, the data extraction component 702 can extract (or otherwise receive) current dynamic system state data 102 regarding the current tasks and operating conditions of the dynamic system. More particularly, the data extraction component 702 can extract the specific features from the dynamic system stat data 102 that have been defined in accordance with the model development and training process as the input parameters of the one or more demand models 138, the one or more TAT models 140 and/or the one or more staffing models 142. For example, the input parameters extracted from the task data 104 can include the currently pending tasks of the dynamic system, the status of the tasks, the locations of the tasks, the priority levels of the tasks, and the like. The input parameters extracted from the operating conditions data 106 can include for example, current operating conditions of the dynamic system (e.g., hospital occupancy levels, bed availability, bed status, bed wait times, staff availability, staff location, supply availability, etc.) and current contextual conditions (e.g., time of day, day of week, weather, externa system events, etc.) associated with the dynamic system. The demand forecasting component 704 can further apply the one or more demand models 140 to the extracted input parameters to generate predictive output data 120 regarding the forecasted task demand. Similarly, the TAT forecasting component 706 can apply the one or more TAT models 140 to the appropriate extracted input parameters to generate predictive output data 120 regarding the forecasted task TAT. Likewise, the staffing forecasting component 708 can apply the one or more staffing models 142 to the appropriate extracted input parameters to generate predictive output data 120 regarding the forecasted number/amount of staff available per shift or timeframe (or another suitable aggregation factor).

FIG. 8 presents an example task management module 122 that employs combinatorial optimization and/or machine learning techniques to manage tasks of a dynamic system based on task demand and/or task TAT in in accordance with one or more embodiments of the disclosed subject matter. The task management module 122 can include regulatory evaluation component 806, notification component 812 and optimization component 814. Repetitive description of like elements employed in respective embodiments is omitted for sake of brevity.

The regulatory evaluation component 806 can be configured to monitor the predictive output data 120 to facilitate compliance with defined requirements or restrictions of the dynamic system. For example, the regulatory evaluation component 806 can access service level agreement (SLA) information 802 for the dynamic system that can include information defining rules, restrictions and/or protocols for operations of the dynamic system, including operations of the tasks. For example, the SLA information 802 can include resource information regarding restrictions or requirements of resources for the tasks, such as information defining type and amount of resources to be used for certain tasks, amount of resource to be made available for certain tasks, and the like. The SLA information 802 can also include information regarding requirements of the TATs for certain tasks or groups of tasks (e.g., grouped by unit, priority type, etc.). For example, hospitals often have defined service level agreements (SLAs) for certain tasks that set maximum TATs for the respective tasks, among other requirements for the tasks. In another example, the SLA information 802 can also provide rules or regulations regarding qualifications of workers for performing certain tasks (e.g., required skill set).

In some embodiments, the resource monitoring component 808 can facilitate determining when the available system resources are insufficient in view of the current and expected demand (e.g., the currently pending and predicted tasks). In this regard, the resource monitoring component 808 can determine the amount and/or type of resources that are needed to satisfy the current and forecasted demand provided in the predictive output data 120. In some implementations, the resource monitoring component 808 can employ SLA information that defines resource requirements/restrictions for the different tasks to facilitate determining the amount and/or type of resources that are needed to satisfy the current and forecasted demand. The resource monitoring component 808 can also employ machine learning techniques to determine the amount and/or type of resources that are needed to satisfy the current and forecasted demand. In some embodiments in which the system employs one or more staffing models 142, the resource monitoring component 808 can further be provided with information included in the predictive output data 120 that identifies the estimated number/amount of staff available to perform tasks within a defined timeframe (e.g., per shift, per hour, etc.). In other implementations, the resource monitoring component 808 can determine staff availability information from other sources providing available system resource information 804. For example, the resource monitoring component 808 can access available system resource information 804 that identifies or otherwise indicates the amount and/or distribution of available resources of the dynamic system. For example, in implementations in which the dynamic system is a hospital and the tasks involve EVS tasks, the available system resource information 804 can include information identifying the EVS staff that are currently working and/or that will be working over the upcoming defined timeframe. The available system resource information 804 can also include information that identifies their skill level, their performance history (e.g., efficiency, quality and proficiency), their current location within the hospital, their current activity (e.g., on task or available, on break, etc.), and the like. The available system resource information 804 can also include information regarding availability and location of supplies and equipment needed for performance of the EVS tasks.

The resource monitoring component 808 can further determine if the expected demand over an upcoming timeframe indicates the available system resources are deficient. For example, the resource monitoring component 808 can determine if the amount and/or type of resources needed to satisfy the estimated demand exceeds those available by a defined threshold or percentage. For instance, the resource monitoring component 808 can determine if the expected number of upcoming tasks for a particular hospital unit over an upcoming timeframe exceeds the exceeds the capacity of the expected number of available staff members in the upcoming timeframe. In some embodiments, the defined threshold or percentage can be defined by or otherwise based on one or more defined SLAs included in the SLA information 802 (e.g., medical unit X requires a minimum of Y workers assigned to the EVS tasks in medical unit X). The notification component 812 can further generate alerts/notification regarding determined shortages in system resources (e.g., demand/TAT notification 128). For example, the notification component 812 can be configured to generate and send an electronic notification to a suitable entity regarding a determination that the available system resources are insufficient given the expected demand.

The resource evaluation component 806 can also include system flow monitoring component 810 to facilitate determining whether the expected demand and/or predicted task TATs indicate a violation or potential violation to a defined SLA requirement included in the SLA information 802. For example, the system flow monitoring component 810 can determine if a forecasted TAT for specific task or group of tasks (e.g., tasks associated with medical unit B, tasks of a specific type etc.) exceeds a maximum allotted TAT for the task or groups of tasks. The notification component 812 can further be configured to generate and send a notification (e.g., a demand/TAT notification 128) to an appropriate entity regarding the violation or potential violation to the SLA requirement.

The task management module 122 can further include optimization 814 to facilitate optimizing performance of the tasks to achieve one or more goals of the dynamic system, such as optimal patient flow, quality of care and resource utilization in implementations in which the dynamic system is a hospital. In this regard, the optimization component can include prioritization component 816, resource allocation component 818 and resource assignment component 820.

The prioritization component 816 can be configured to determine how to prioritize and order tasks of the dynamic system based at least in part on the predictive output data 120. For example, the prioritization component 816 can determine an optimal prioritization order/sequence for the currently pending (and optionally the predicted) tasks based on the forecasted demand (e.g., the predicted distribution of tasks) and/or the predicted TATs for the currently pending (and optionally the predicted tasks). In various embodiments, the prioritization component 816 can employ machine learning and/or combinatorial optimization techniques to determine the optimal prioritization order as a function of that which minimizes the TATs for the tasks (e.g., the currently pending and/or the predicted tasks). The task prioritization combinatorial optimization function can also factor additional constraints, such as system defined requirements for prioritizing certain tasks with specified attributes and/or defined requirements for task TATs included in the SLA information 802. With these embodiments, the combinatorial optimization function can also account for such additional constraints on the maximum allowed TATs for certain tasks. The combinatorial optimization function can factor other defined system constraints regarding patient flow, operating constraints, quality of care requirements, and the like. In some implementations, the combinatorial optimization function can also factor in the predicted demand in association with determining the prioritization order for the currently pending/predicted tasks. For example, based on a predicted high demand for beds in a particular unit of a hospital, the prioritization order can prioritize performance of currently pending bed cleaning tasks in that unit before currently pending tasks in a lower demand unit to prevent or minimize system bottlenecks. The prioritization component 816 (and/or the notification component 812) can further provide information regarding the optimal determined prioritization scheme (e.g., task prioritization information 130) to one or more appropriate entities for use in association with real-time management of the tasks. For example, in some implementations, the prioritization component 816 can provide the task prioritization information 130 to respective EVS workers at the hospital via one or more devices accessible to the EVS works (e.g., personal computing devices, a communal monitor at the hospital, etc.). The EVS workers can further follow the prescribed prioritization scheme based on reception of the task prioritization information 130.

The resource allocation component 818 can provide for determining an optimal allocation of available system resources for the tasks (e.g., the currently pending and/or predicted task), based on the predicted demand, the predicted TATs, the estimated staff availability, predicted SLA violations, and/or any defined resource requirements for the tasks (e.g., provided by the SLA information 804). In this regard, the resource allocation component 818 can determine how to optimize resource allocation based on the current constraints of the system, defined rules of the system, and an optimization objective for the system, such as increasing throughput, maximizing the number of tasks performed, equalizing the distribution of the workload amongst available staff, and the like. The system constraints can include assignment constraints, shift constraints, capacity constraints and the like. The resource allocation rules can include for example, assignment rules, fair distribution of task rules, SLA rules, zone rules, patient and material transport rules, and the like.

In various embodiments, the resource allocation component 818 can employ machine learning and/or combinatorial techniques to determine how to allocate the available system resources to the tasks to minimize the TATs, meet defined requirements for the task regarding resource utilization for certain tasks (e.g., number of allocated resources, type of allocated resources, location of allocated resources, etc.), maximize the number of jobs fulfilled, balance the distribution of the workload amongst available workers, and to achieve optimal patient flow. For example, in implementations in which the dynamic system is a hospital and the tasks managed include EVS tasks, the system can employ machine learning and/or combinatorial optimization to determine how to allocate the available system resources (e.g., number of workers to assign to a task or group of tasks grouped by unit, type, etc., amount/type of supplies to distribute for the respective tasks, etc.) by determining and selecting a resource allocation scheme that facilities minimizing the TATs, meeting the expected demand, minimizing bottlenecks, and/or meeting defined requirements for the resources associated with certain tasks. In this regard, the resource allocation component 818 can determine the amount and/or type of system resources needed to fulfill the currently pending tasks and the predicted tasks (e.g., EVS tasks per unit) for the next N hours and allocate the available system resources accordingly. In addition to meeting current and expected demand, the resource allocation component 818 can also allocate the available system resources to minimize the predicted TATs and meet defined SLAs. The resource allocation component 818 (and/or the notification component 812) can further provide information regarding the optimal determined resource allocation scheme (e.g., resource allocation information 132) to one or more suitable entities responsible for managing distribution of the available system resources.

For example, consider a system with a set number of resources (I), a set number of jobs (J), and a set number of time periods (T). In one embodiment, the resource allocation component 818 can employ a combinatorial optimization problem that facilitate determining how to allocate resources and/or assign resources to tasks based on the following defined parameters, decision variables and constraints.

Parameters:
$N^t$ Number of resources at time t,
$J^t$ Number of jobs at time t,
$L_j$ Job duration for job j,
$P_j$ Penalty for unfulfilled job j,
$R_j$ Reward for fulfilled job j,
$C_i$ Penalty for unequal load distribution for resource I,
$U_t$ Max jobs to assign per resource,
$M_i$ jobs to assign per resource, and
$S_i$ Remaining duration until shift end for resource i.

Decision variables:
$y_{ijt}$ Resource i fulfills job j at time t
$u_j$ Unassigned job
$d_{it}^-$ Deviation from $$\frac{N_t}{J_t}$$

measured for equal distribution of load for resource i
$d_{it}^+$ Deviation from $$\frac{N_t}{J_t}$$

measured for equal distribution of load for resource i

In accordance with this example, the resource allocation component can employ an optimization problem that aims to determine how to allocate resources with an objective of maximizing the rewards minus the penalties expressed mathematically by Equation 1 below with the following constraints.

$$\text{Maximize } \Sigma_i \Sigma_j \Sigma_t R_{jk} y_{ijkt} - \Sigma_j P_j u_j - \Sigma_i \Sigma_t C_{it} d_{it}^- - \Sigma_i \Sigma_t C_{it} d_{it}^+ \quad \text{(Equation 1)}$$

Constraints:
A resource is assigned to only one job at any given time $\sum_j y_{ijt} \leq 1 \forall i \forall t$ A job is assigned to only one resource at any given time $\sum_i y_{ijt} \leq 1 \forall j \forall t$ Indicator to indicate a new job j is assigned to resource i at time t $y_{ijt+1} + y_{ij't} \leq z_{ijt+1} + 1 j \neq j' \forall j \forall i \forall t$ $z_{iit} \geq y_{iit}$ $u_j + \sum_i \sum_t z_{iit} = 1$ Assigned job must be completed before another job is assigned to same resource $\sum_e t^{ij} y_{ijt} = L_j z_{ijt} \forall i \forall t$ Max and Min number of jobs assigned to a resource $U_i \leq \sum_i \sum_t z_{ijt} \leq M_i \forall i$ Shift constraints $\sum_j \sum_t y_{ijt} \leq s_i \forall i$ Equal job distribution among resources $$m_{it} = \frac{\sum_j \sum_t z_{ijt}}{t} \quad \forall i \forall t$$

$$\frac{N_t}{J_t} = m_{it} + d_{it}^- - d_t^+ \quad \forall i \forall t$$

The resource assignment component 820 can also determine how to assign specific workers/staff to specific jobs based on the predicted distributed of tasks (i.e., the predicted demand) and/or the predicted TATs for the currently pending and/or predicted tasks. With these embodiments, the resource assignment component 820 can also employ one or more machine learning and/or combinatorial optimization techniques to determine who to assign to specific tasks to minimize the TATs, meet the expected demand, minimize bottlenecks, and/or meet defined requirements for the resources associated with certain tasks. In this regard, the resource assignment component 820 can determine the best available person for each job based on their skill level, performance efficiency and quality with certain jobs, location, fatigue level, etc., that results in minimizing the TATs and forecasted demand while also meeting any defined SLAs for the jobs (e.g., required skill level or personnel qualification). In some embodiments, information regarding individual staff skill sets, qualifications and/or performance metrics can be provided in the available system resource information 804.

In various embodiments, the optimization component 814 can employ machine learning to determine the optimal prioritization order for the tasks, the optimal allocation of available system resources, and/or the optimal assignment of specific resources matched to specific tasks to minimize the TATs and meet the expected demand using combinatorial optimization and/or machine learning. With these embodiments, the determinations and/or inferences regarding optimal task prioritization, resource allocation and/or resource assignment can be based on entirety or a subset of the historical state data 204. The optimization component 814 can employ various classification (explicitly and/or implicitly trained) schemes and/or systems (e.g., support vector machines, neural networks, expert systems, Bayesian belief networks, fuzzy logic, data fusion engines, etc.) in connection with inferring the task prioritization information 130, the resource allocation information 132 and/or the resource assignment information 134 based on a current state of the dynamic system. A classifier can map an input attribute vector, x=(x1, x2, x4, x4, xn), to a confidence that the input belongs to a class, such as by f(x)=confidence (class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 9:
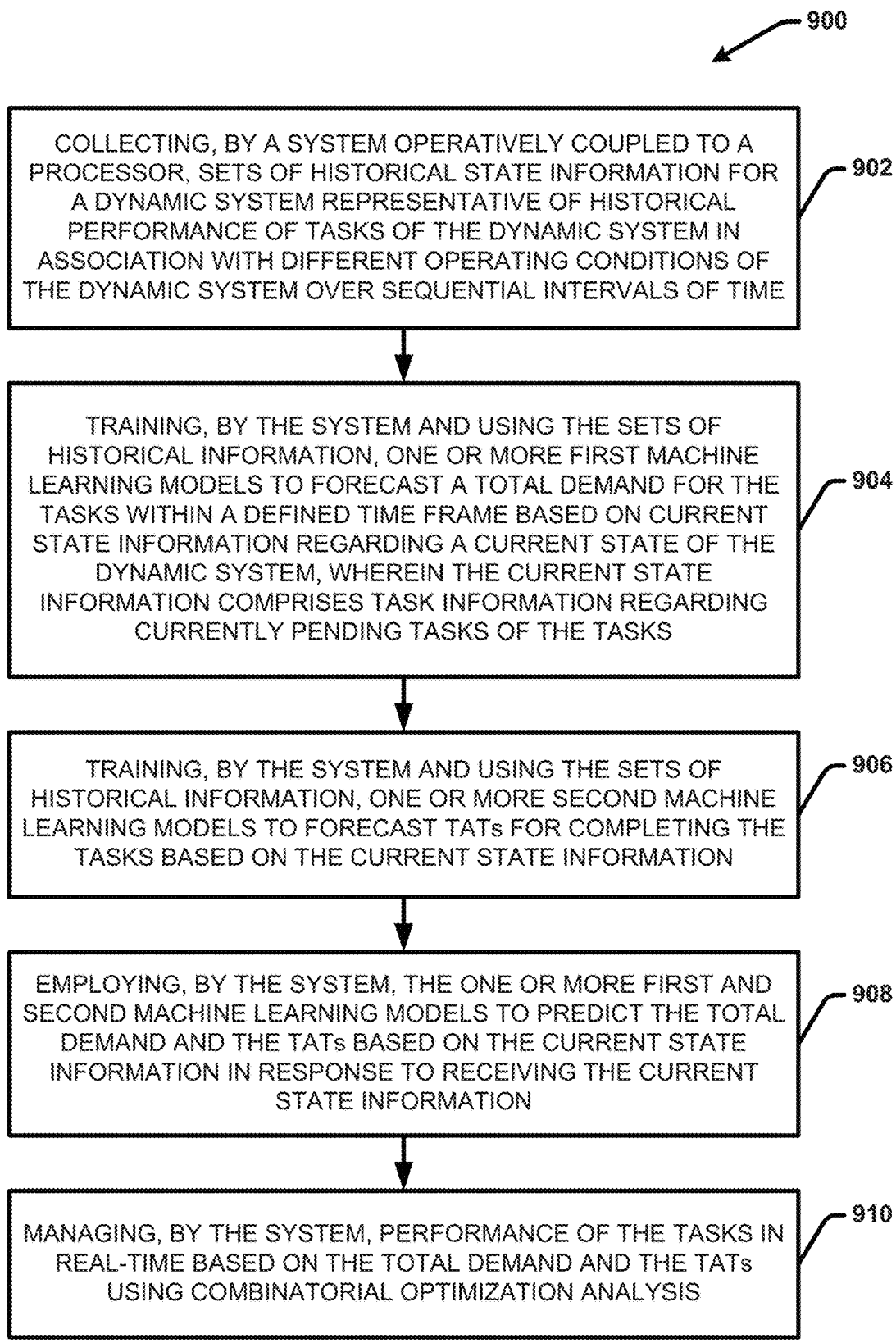
FIG. 9 illustrates an example, high-level flow diagram of a computer-implemented process for managing tasks of a dynamic system with limited resources using a machine-learning and combinatorial optimization framework in accordance with one or more embodiments of the disclosed subject matter.

FIG. 9 illustrates an example, high-level flow diagram of a computer-implemented process 900 for managing tasks of a dynamic system with limited resources using a machine-learning and combinatorial optimization framework in accordance with one or more embodiments of the disclosed subject matter. Repetitive description of like elements employed in respective embodiments is omitted for sake of brevity.

At 902, a system operatively coupled to a processor (e.g., system 100 or the like), collects (e.g., by the task management model development module 110 using data collection component 302) sets of historical state information for a dynamic system representative of historical performance of tasks of the dynamic system in association with different operating conditions of the dynamic system over sequential intervals of time. At 904, the system can train (e.g., using total demand ML component 304), using the sets of historical state information, one or more first machine learning model (e.g., the one or more total demand models 138) to forecast a total demand for the tasks within a defined time frame based on current state information regarding a current state of the dynamic system, wherein the current state information comprises task information regarding currently pending tasks of the tasks. At 906, the system can also train (e.g., using the TAT ML component 306) one or more second machine learning models on the sets of historical state information to forecast TATs for completing the tasks based on the current state information.

For example, the data collection component 302 can regularly (e.g., every N minutes) collet sets of the dynamic system state data 102, wherein each set corresponds to state information that was generated over a defined time period. In this regard, with respect to a hospital system, the data collection component 302 can collect data every 30 minutes, every hour, etc., information regarding the tasks that were scheduled, the tasks that were performed, timing of performance, the attributes of the tasks, the operating condition of the hospital, and the like and. Each set can thus represent a historical snapshot in time of the hospital operations and can be used to learn correlations between different operating condition parameters on task TATs and demand for the tasks. In various embodiments, the task management model development module 110 can regularly and/or continuously train and update the demand forecasting and TAT forecasting models based on new sets of historical state information as they are collected over the sequential intervals of time.

At 908, the system can further employ the one or more first and second machine learning models to predict the total demand and the TATs based on the current state information in response to receiving the current state information (e.g., using demand forecasting component 802 and the TAT forecasting component 804 respectively). In various embodiments, model training and development can continue to occur simultaneously as previously developed/trained versions of the total demand and TAT models are used in real-time to predict total demand and TAT based on current state information. At 910, the system can further manage (e.g., by the task management module 122) performance of the tasks in real-time based on the total demand and the TATs using combinatorial optimization analysis. For example, based on the total demand and/or the TATs, the task management module 122 can perform various task management optimization functions, including but not limited to: determining whether any of the TATs fail to comply with a defined service requirement; determining whether available resources of the dynamic system are sufficient; determining a prioritization order for performing the currently pending tasks; determining an allocation of the available resources to the tasks; and determining an assignment of specific resources of the available resources to specific tasks of the tasks.

Figure 10:
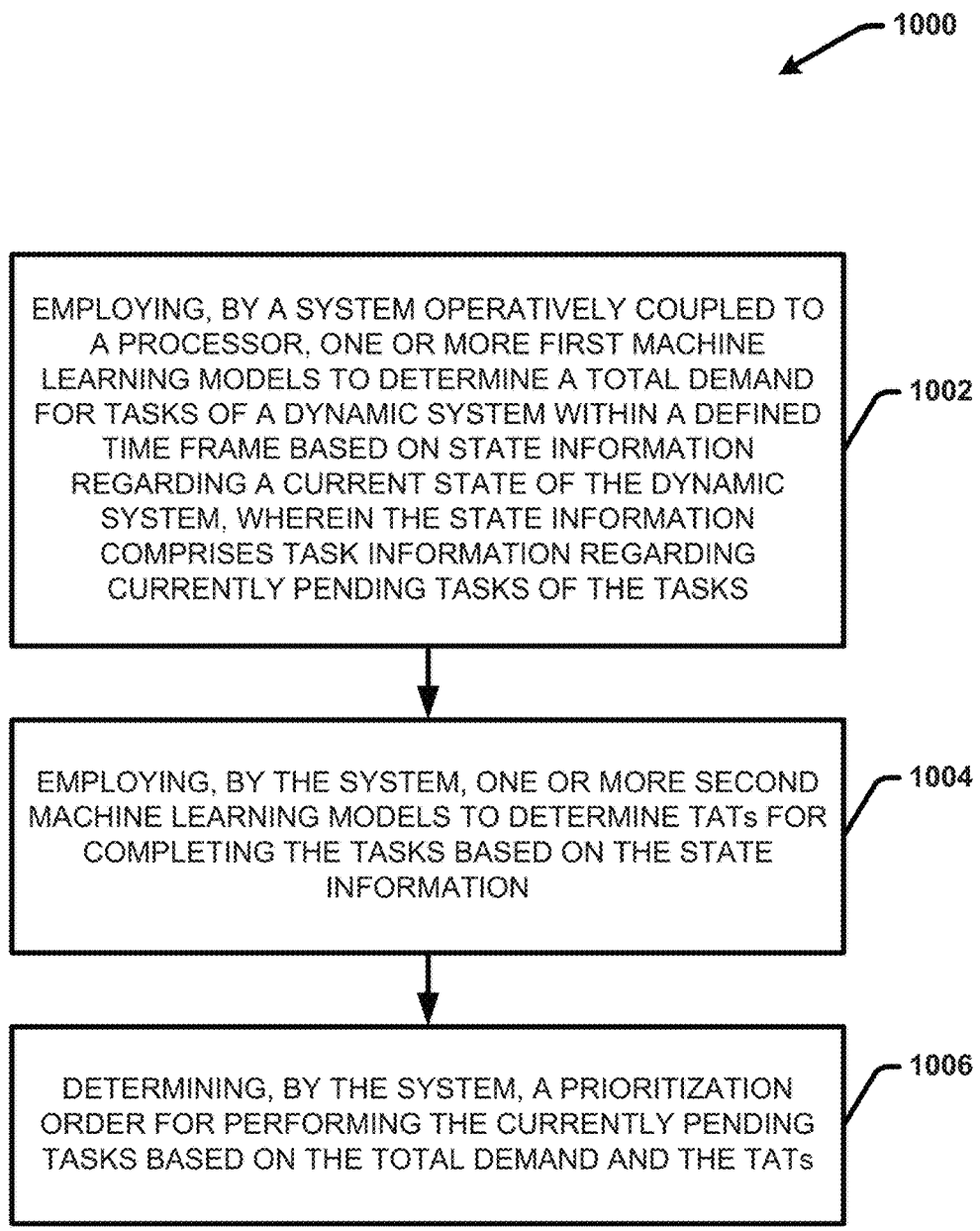
FIG. 10 illustrates another example, high-level flow diagram of a computer-implemented process for managing tasks of a dynamic system with limited resources using a machine-learning and combinatorial optimization framework in accordance with one or more embodiments of the disclosed subject matter.

FIG. 10 illustrates another example, high-level flow diagram of a computer-implemented process 1000 for managing tasks of a dynamic system with limited resources using a machine-learning and combinatorial optimization framework in accordance with one or more embodiments of the disclosed subject matter. Repetitive description of like elements employed in respective embodiments is omitted for sake of brevity.

At 1002, a system operatively coupled to a processor (e.g., system 100 or the like), employs (e.g., using model application module 116) one or more first machine learning models (e.g., one or more total demand models 138) to determine a total demand for tasks of a dynamic system within a defined time frame based on state information (e.g., dynamic system state data 102) regarding a current state of the dynamic system, wherein the state information comprises task information regarding currently pending tasks of the tasks. At 1004, the system employs (e.g., using model application module 116) one or more second machine learning models (e.g., one or more TAT models 140) to determine TATs for completing the tasks based on the state information. At 1006, the system determines a prioritization order for performing the currently pending tasks based on the total demand and the TATs (e.g., using task management module 122, or more particularly using prioritization component 912).

Figure 11:
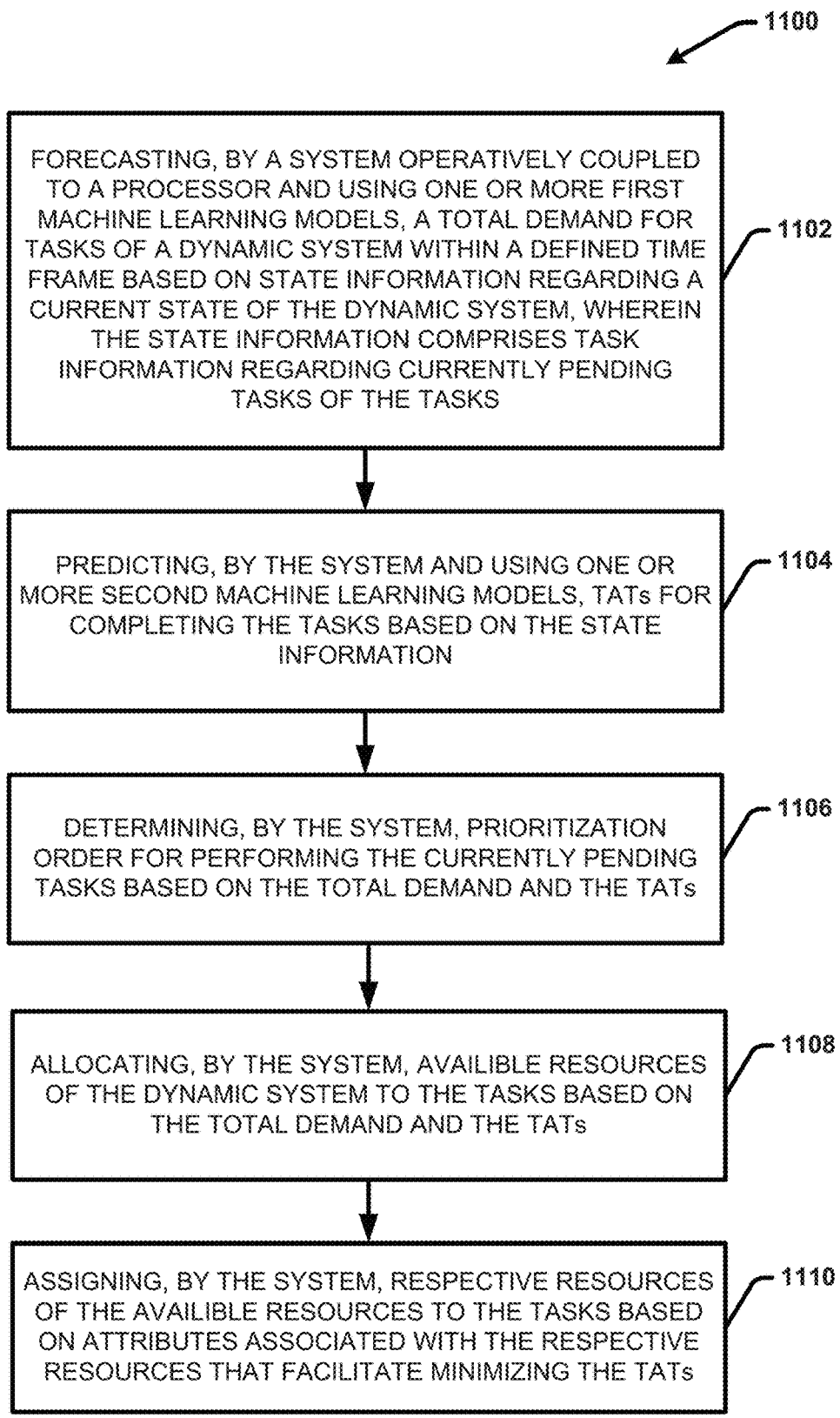
FIG. 11 illustrates another example, high-level flow diagram of a computer-implemented process for managing tasks of a dynamic system with limited resources using a machine-learning and combinatorial optimization framework in accordance with one or more embodiments of the disclosed subject matter.

FIG. 11 illustrates another example, high-level flow diagram of a computer-implemented process 1100 for managing tasks of a dynamic system with limited resources using a machine-learning and combinatorial optimization framework in accordance with one or more embodiments of the disclosed subject matter. Repetitive description of like elements employed in respective embodiments is omitted for sake of brevity.

At 1102, a system operatively coupled to a processor (e.g., system 100 or the like), forecasts (e.g., using model application module 126), using one or more first machine learning models (e.g., one or more total demand models 138), a total demand for tasks of a dynamic system within a defined time frame based on state information regarding a current state of the dynamic system (e.g., dynamic system state data 102), wherein the state information comprises task information regarding currently pending tasks of the tasks. At 1104, the system predicts (e.g., using model application module 126), using one or more second machine learning models (e.g., one or more TAT models 140), TATs for completing the tasks based on the state information. At 1106, the system determines a prioritization order for performing the currently pending tasks based on the total demand and the TATs (e.g., using task management module 122, or more particularly using prioritization component 912). At 1108, the system allocates available resources of the dynamic system to the tasks based on the total demand and the TATs (e.g., using task management module 122, or more particularly using resource allocation component 914). For example, in implementations in which the dynamic system is a hospital, the task management module 122 can allocate amounts of the available resources to respective hospital units (e.g., Unit A needs 3 staff, unit B needs 1 staff, etc.) based on the total demand in each unit (e.g., determined based on the currently pending jobs and the predicted jobs per unit), and the TATs for the EVS jobs in each hospital unit (e.g., the TATs for the currently pending and the predicted jobs). At 1110, the system can assign respective resources of the available resources to the tasks based on attributes associated with the respective resources that facilitate minimizing the TATs. For instance, further to the hospital example, the task management module 122 can assign employee Anna to tasks of type A as opposed to tasks of type B because Anna has demonstrated superior performance efficiency in performing task of type A as opposed to tasks of type B.

Figure 12:
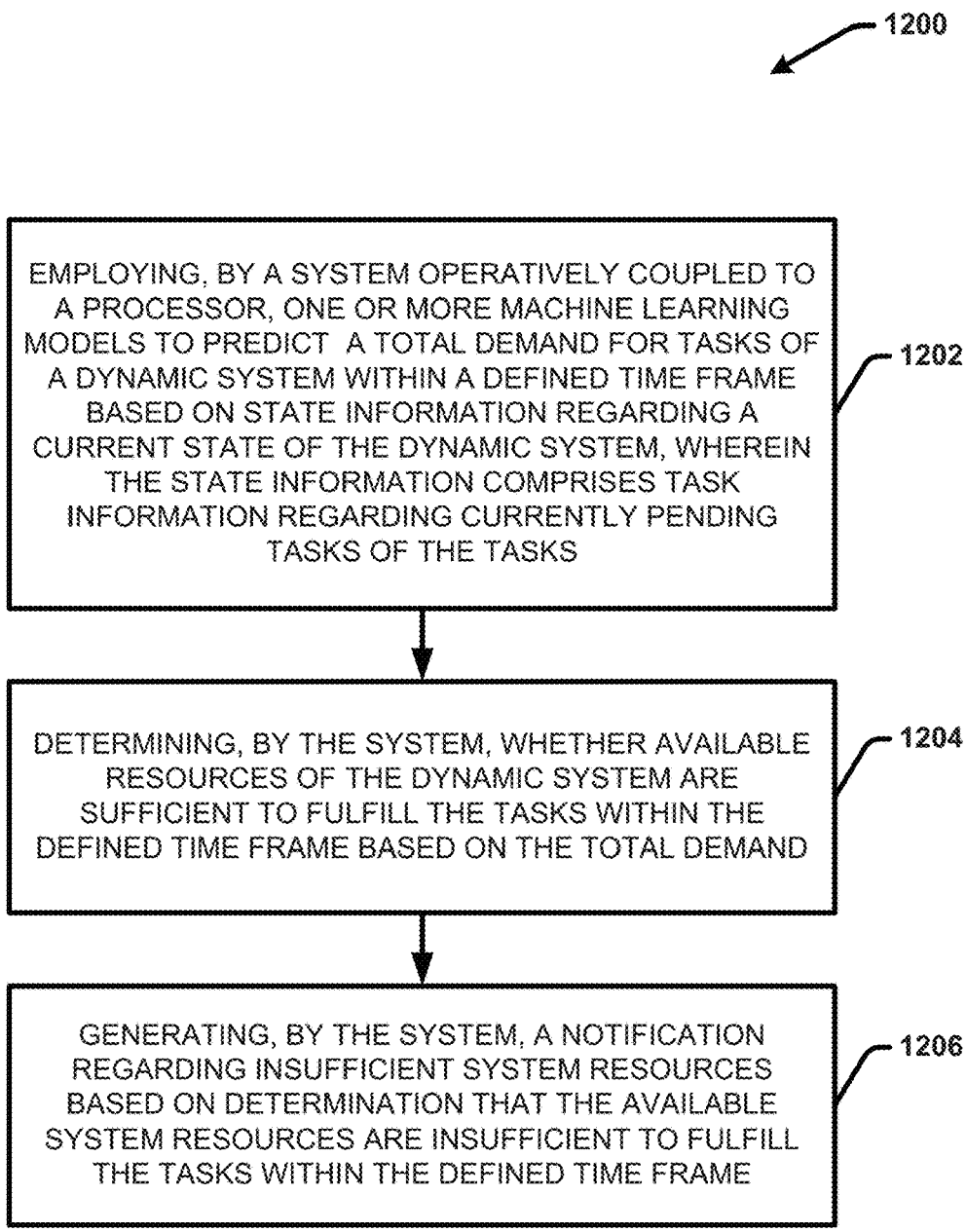
FIG. 12 illustrates another example, high-level flow diagram of a computer-implemented process for managing tasks of a dynamic system with limited resources using a machine-learning and combinatorial optimization framework in accordance with one or more embodiments of the disclosed subject matter.

FIG. 12 illustrates another example, high-level flow diagram of a computer-implemented process 1200 for managing tasks of a dynamic system with limited resources using a machine-learning and combinatorial optimization framework in accordance with one or more embodiments of the disclosed subject matter. Repetitive description of like elements employed in other embodiments described herein is omitted for sake of brevity.

At 1202, a system operatively coupled to a processor (e.g., system 100 or the like), employs (e.g., using model application module 116) one or more machine learning models (e.g., one or more total demand models 138) to determine a total demand for tasks of a dynamic system within a defined time frame based on state information (e.g., dynamic system state data 102) regarding a current state of the dynamic system, wherein the state information comprises task information regarding currently pending tasks of the tasks. At 1204, the system determines whether available resources of the dynamic system are sufficient to fulfill the tasks within the defined time frame based on the total demand (e.g., using resource monitoring component 904). At 1206, the system generates a notification component that generates a notification regarding insufficient system resources based on determination that the available system resources are insufficient to fulfill the tasks within the defined time frame (e.g., using notification component 908).

Figure 13:
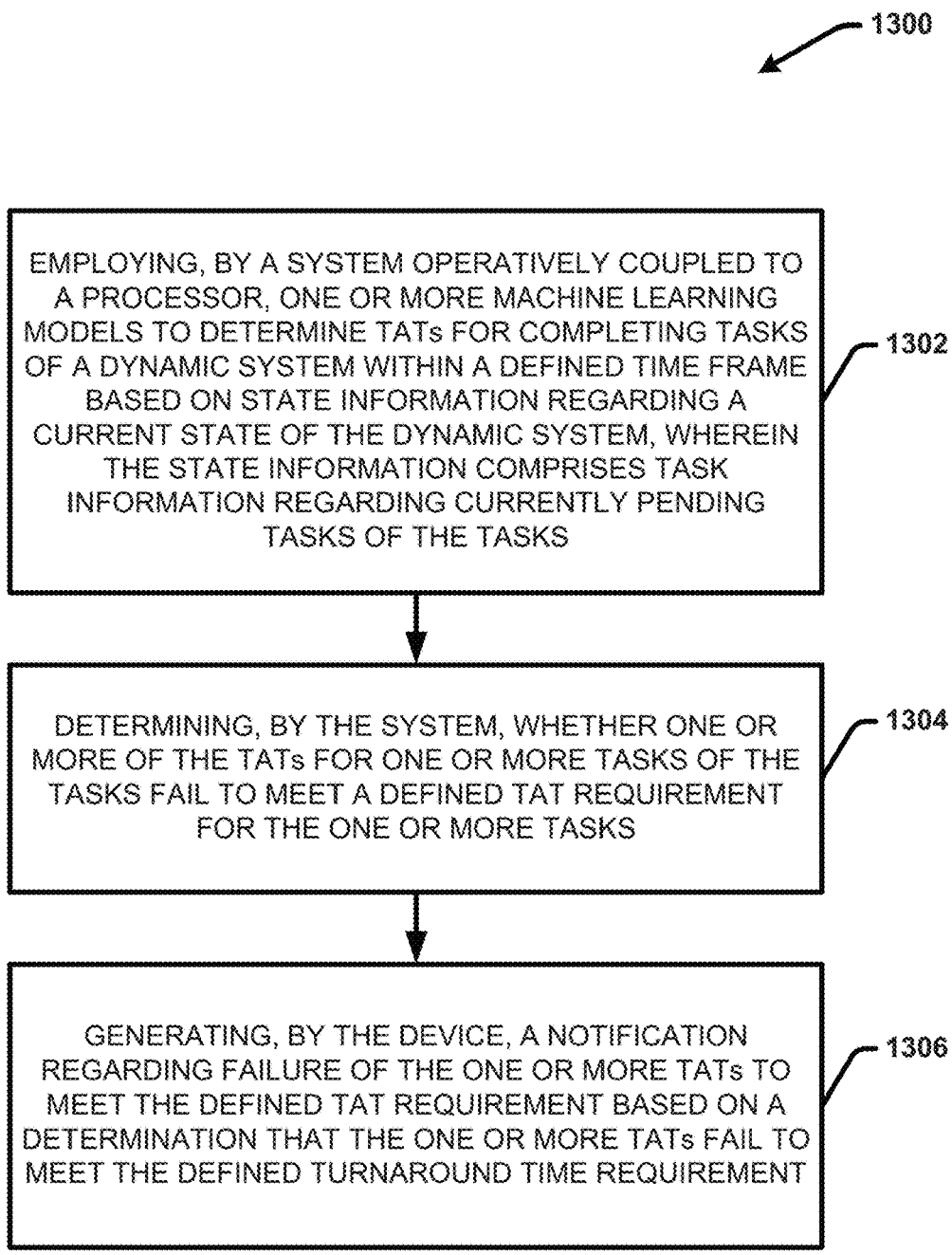
FIG. 13 illustrates another example, high-level flow diagram of a computer-implemented process for managing tasks of a dynamic system with limited resources using a machine-learning and combinatorial optimization framework in accordance with one or more embodiments of the disclosed subject matter.

FIG. 13 illustrates another example, high-level flow diagram of a computer-implemented process 1300 for managing tasks of a dynamic system with limited resources using a machine-learning and combinatorial optimization framework in accordance with one or more embodiments of the disclosed subject matter. Repetitive description of like elements employed in other embodiments described herein is omitted for sake of brevity.

At 1302, a system operatively coupled to a processor (e.g., system 100 or the like), employs (e.g., using model application module 116) one or more machine learning models (e.g., one or more TAT models 140) to determine a total demand for tasks of a dynamic system within a defined time frame based on state information (e.g., dynamic system state data 102) regarding a current state of the dynamic system, wherein the state information comprises task information regarding currently pending tasks of the tasks. At 1304, the system determines whether one or more of the TATs for one or more tasks of the tasks fail to meet a defined TAT requirement for the one or more tasks (e.g., using system flow monitoring component 906). At 1306, the system generates a notification component that generates a notification regarding failure of the one or more TATs to meet the defined turnaround time requirement based on a determination that the one or more TATs fail to meet the defined TAT requirement (e.g., using notification component 908).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 14, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 14:
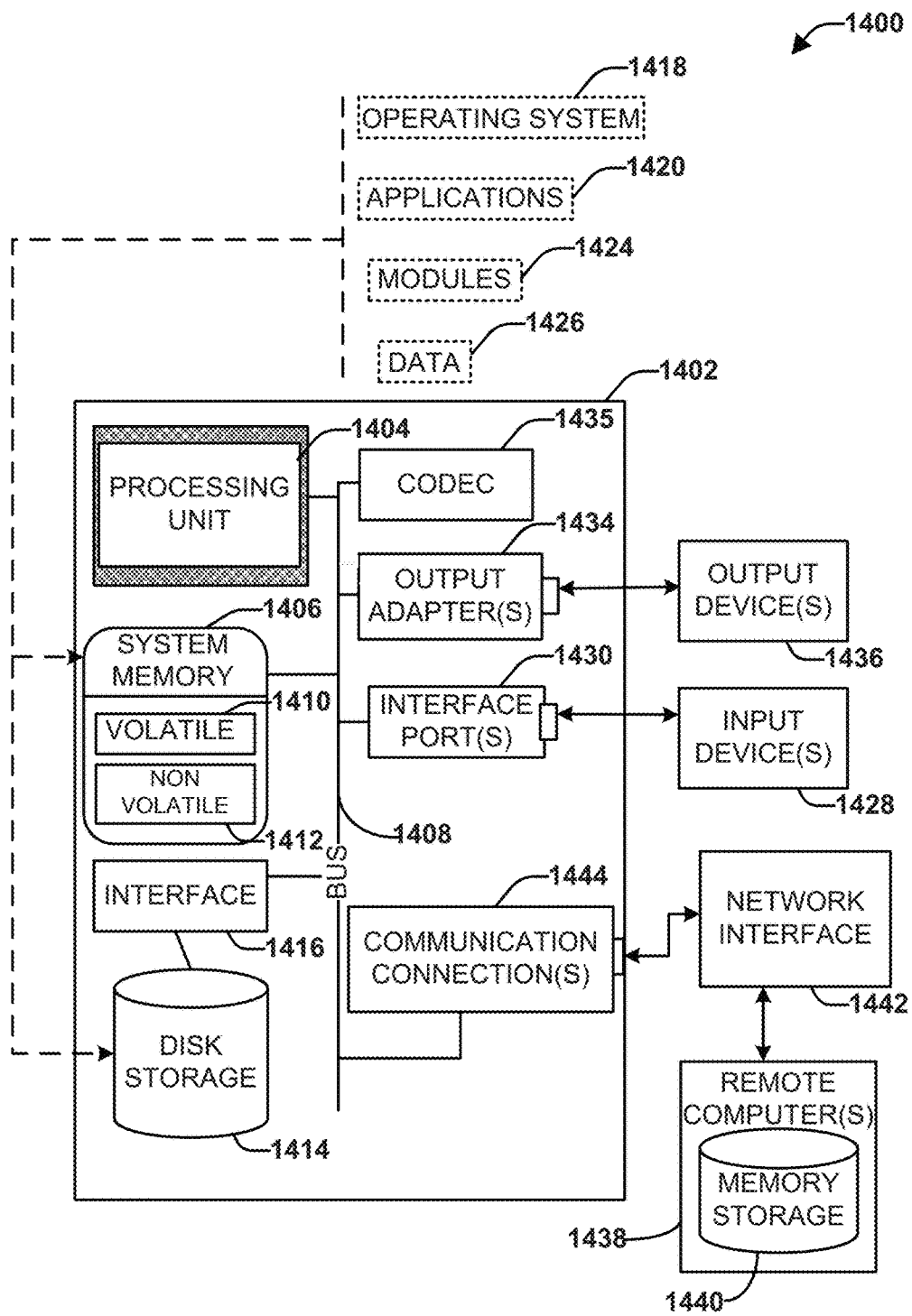
FIG. 14 illustrates a block diagram of an example, non-limiting operating environment in which one or more embodiments described herein can be facilitated.

With reference to FIG. 14, an example environment 1400 for implementing various aspects of the claimed subject matter includes a computer 1402. The computer 1402 includes a processing unit 1404, a system memory 1406, a codec 1435, and a system bus 1408. The system bus 1408 couples system components including, but not limited to, the system memory 1406 to the processing unit 1404. The processing unit 1404 can be any of various available processors. Dual microprocessors and other multiprocessor architectures also can be employed as the processing unit 1404.

The system bus 1408 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13144), and Small Computer Systems Interface (SCSI).

The system memory 1406 includes volatile memory 1410 and non-volatile memory 1412, which can employ one or more of the disclosed memory architectures, in various embodiments. The basic input/output system (BIOS), containing the basic routines to transfer information between elements within the computer 1402, such as during start-up, is stored in non-volatile memory 1412. In addition, according to present innovations, codec 1435 can include at least one of an encoder or decoder, wherein the at least one of an encoder or decoder can consist of hardware, software, or a combination of hardware and software. Although, codec 1435 is depicted as a separate component, codec 1435 can be contained within non-volatile memory 1412. By way of illustration, and not limitation, non-volatile memory 1412 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1412 can employ one or more of the disclosed memory devices, in at least some embodiments. Moreover, non-volatile memory 1412 can be computer memory (e.g., physically integrated with computer 1402 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1410 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1402 can also include removable/non-removable, volatile/non-volatile computer storage medium. FIG. 14 illustrates, for example, disk storage 1414. Disk storage 1414 includes, but is not limited to, devices like a magnetic disk drive, solid state disk (SSD), flash memory card, or memory stick. In addition, disk storage 1414 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1414 to the system bus 1408, a removable or non-removable interface is typically used, such as interface 1416. It is appreciated that disk storage 1414 can store information related to an entity. Such information might be stored at or provided to a server or to an application running on an entity device. In one embodiment, the entity can be notified (e.g., by way of output device(s) 1436) of the types of information that are stored to disk storage 1414 or transmitted to the server or application. The entity can be provided the opportunity to opt-in or opt-out of having such information collected or shared with the server or application (e.g., by way of input from input device(s) 1428).

It is to be appreciated that FIG. 14 describes software that acts as an intermediary between entities and the basic computer resources described in the suitable operating environment 1400. Such software includes an operating system 1418. Operating system 1418, which can be stored on disk storage 1414, acts to control and allocate resources of the computer system 1402. Applications 1420 take advantage of the management of resources by operating system 1418 through program modules 1424, and program data 1426, such as the boot/shutdown transaction table and the like, stored either in system memory 1406 or on disk storage 1414. It is to be appreciated that the claimed subject matter can be implemented with various operating systems or combinations of operating systems.

An entity enters commands or information into the computer 1402 through input device(s) 1428. Input devices 1428 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1404 through the system bus 1408 via interface port(s) 1430. Interface port(s) 1430 include, for example, a serial port, a parallel port, a game port, and a universal serial bus (USB). Output device(s) 1436 use some of the same type of ports as input device(s) 1428. Thus, for example, a USB port can be used to provide input to computer 1402 and to output information from computer 1402 to an output device 1436. Output adapter 1434 is provided to illustrate that there are some output devices 1436 like monitors, speakers, and printers, among other output devices 1436, which require special adapters. The output adapters 1434 include, by way of illustration and not limitation, video and sound cards that provide a means of connection between the output device 1436 and the system bus 1408. It should be noted that other devices or systems of devices provide both input and output capabilities such as remote computer(s) 1438.

Computer 1402 can operate in a networked environment using logical connections to one or more remote computers, such as remote computer(s) 1438. The remote computer(s) 1438 can be a personal computer, a server, a router, a network PC, a workstation, a microprocessor based appliance, a peer device, a smart phone, a tablet, or other network node, and typically includes many of the elements described relative to computer 1402. For purposes of brevity, only a memory storage device 1440 is illustrated with remote computer(s) 1438. Remote computer(s) 1438 is logically connected to computer 1402 through a network interface 1442 and then connected via communication connection(s) 1444. Network interface 1442 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1444 refers to the hardware/software employed to connect the network interface 1442 to the system bus 1408. While communication connection 1444 is shown for illustrative clarity inside computer 1402, it can also be external to computer 1402. The hardware/software necessary for connection to the network interface 1442 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor that executes the computer executable components stored in the memory, wherein the computer executable components comprise:
        a collection component that collects sets of state information for a healthcare facility every predefined time interval over a course of operation of the healthcare facility and stores the sets in a machine learning database, the sets of state information comprising operating conditions data regarding operating conditions of the healthcare facility over each predefined time interval and task data regarding pending housekeeping tasks and performed housekeeping tasks over each predefined time interval;
        a demand forecasting component that employs one or more demand forecasting models developed using a first machine learning processes to estimate, every predefined time interval, an expected demand for an upcoming group of housekeeping tasks of the healthcare facility for performance over a defined upcoming time frame based on a most recently collected set of the sets;
        a turnaround time forecasting component that employs one or more turnaround time forecasting models developed using a second machine learning processes to estimate, every predefined time interval, expected turnaround times for completing respective housekeeping tasks of the upcoming group over the defined upcoming timeframe based on the most recently collected set;
        a prioritization component that determines a prioritization framework for performing the respective housekeeping tasks of the upcoming group based on the expected demand and the expected turnaround times; and
        a model development component that regularly retrains the one or more demand forecasting models using the sets of state information and the first machine learning process to forecast future demands for housekeeping tasks of the healthcare facility based on changes in the operating condition data and the task data, and regularly retrains the one or more turnaround round time forecasting models using the sets of state information and the second machine learning process to forecast expected turnaround times for completing the housekeeping tasks based on the changes.

2. The system of claim 1, wherein the model development component retrains the one or more demand forecasting models and the one or more turnaround time forecasting models in a cyclic manner in accordance with sequential training cycles and using a group of the sets received after a previous training cycle of the sequential training cycles.

3. The system of claim 1, wherein the model development component generates updated demand forecasting models and updated turnaround time forecasting models as a result of the retraining and wherein the demand forecasting component and the turnaround time forecasting component respectively employ the updated demand forecasting models and the updated turnaround time forecasting models.

4. The system of claim 1, wherein the predefined time interval comprises every 30 minutes or every hour.

5. The system of claim 1, wherein the prioritization component determines the prioritization framework as a function of combinatorial optimization problem that minimizes the expected turnaround times.

6. The system of claim 1, wherein the computer executable components further comprise:
    a resource allocation component that allocates available resources of the healthcare facility to the respective housekeeping tasks based on the expected demand and the expected turnaround times.

7. The system of claim 1, wherein the computer executable components further comprise:
a resources allocation component that allocates available resources of the healthcare facility to the respective housekeeping tasks using an optimization function that minimizes the expected turnaround times.

8. The system of claim 1, wherein the expected demand reflects a total distribution of the respective housekeeping tasks for performance within the defined upcoming time frame, and a total distribution of resources required for fulfilling the respective housekeeping tasks within the defined upcoming time frame.

9. The system of claim 8, wherein the computer executable components further comprise:
a resources allocation component that allocates available resources of the healthcare facility to the respective housekeeping tasks using an optimization function that minimizes an imbalance between the available resources of the healthcare facility and the total distribution of resources required for fulfilling the respective housekeeping tasks within the defined upcoming time frame.

10. The system of claim 1, wherein the computer executable components further comprise:
a resource assignment component that assigns respective resources of available resources of the healthcare facility to the respective housekeeping tasks based on attributes associated with the respective resources that facilitate minimizing the expected turnaround times.

11. The system of claim 10, wherein the respective resources include employees and wherein the attributes include skill sets respectively associated with the employees.

12. The system of claim 1, wherein the computer executable components further comprise:
a system flow monitoring component that determines whether one or more of the expected turnaround times for one or more tasks of the respective housekeeping tasks fail to meet a defined turnaround time requirement for the one or more tasks; and
a notification component that generates a notification regarding failure of the one or more turnaround times to meet the defined turnaround time requirement based on a determination that the one or more turnaround times fail to meet the defined turnaround time requirement.

13. The system of claim 1, wherein the computer executable components further comprise:
a resource monitoring component that determines whether available resources of the healthcare facility are sufficient to fulfill the respective housekeeping tasks within the defined upcoming time frame based on the expected demand; and
a notification component that generates a notification regarding insufficient system resources based on determination that the available resources are insufficient to fulfill the respective housekeeping tasks within the defined upcoming time frame.

14. A method, comprising:
collecting, by a system operatively coupled to a processor, sets of state information for a healthcare facility every predefined time interval over a course of operation of the healthcare facility, the sets of state information comprising operating conditions data regarding operating conditions of the healthcare facility over each predefined time interval and task data regarding pending housekeeping tasks and performed housekeeping tasks over each predefined time interval;
employing, by the system, one or more demand forecasting models developed using a first machine learning processes to estimate, every predefined time interval, an expected demand for an upcoming group of housekeeping tasks of the healthcare facility for performance over a defined upcoming time frame based on a most recently collected set of the sets;
employing, by the system, one or more turnaround time forecasting models developed using a second machine learning processes to estimate, every predefined time interval, expected turnaround times for completing respective housekeeping tasks of the upcoming group over the defined upcoming timeframe based on the most recently collected set;
determining, by the system, a prioritization framework for performing respective housekeeping tasks of the upcoming group based on the expected demand and the expected turnaround times;
regularly retraining, by the system the one or more demand forecasting models using the sets of state information and the first machine learning process to forecast future demands for housekeeping tasks of the healthcare facility based on changes in the operating condition data and the task data; and
regularly retraining, by the system, the one or more turnaround time forecasting models using the sets of state information and the second machine learning process to forecast expected turnaround times for completing the housekeeping tasks based on the changes.

15. The method of claim 14, wherein the regularly retraining comprises retraining the one or more demand forecasting models and the one or more turnaround time forecasting models in a cyclic manner in accordance with sequential training cycles and using a group of the sets received after a previous training cycle of the sequential training cycles.

16. The method of claim 14, wherein the regularly retraining results in updated demand forecasting models and updated turnaround time forecasting models, wherein the employing the one or more turnaround time forecasting models comprises employing the updated demand forecasting models, and wherein the employing the one or more turnaround time forecasting models comprises employing the updated turnaround time forecasting models.

17. The method of claim 14, wherein the predefined time interval comprises every 30 minutes or every hour.

18. The method of claim 14, wherein the determining the prioritization framework comprises determining the prioritization framework as a function of a combinatorial optimization problem that minimizes the expected turnaround times.

19. The method of claim 14, further comprising:
allocating, by the system, available resources of the healthcare facility to the respective housekeeping tasks based on the expected demand and the expected turnaround times.

20. The method of claim 14, further comprising:
allocating, by the system, available resources of the healthcare facility to the respective housekeeping tasks using an optimization function that minimizes the expected turnaround times.

21. The method of claim 14, wherein the expected demand reflects a total distribution of the respective housekeeping tasks for performance within the defined upcoming time frame, and a total distribution of resources required for fulfilling the respective housekeeping tasks within the defined upcoming time frame.

22. The method of claim 21, further comprising:
allocating, by the system, available resources of the healthcare facility to the respective housekeeping tasks using an optimization function that minimizes an imbalance between the available resources of the healthcare facility and the total distribution of resources required for fulfilling the respective housekeeping tasks within the defined upcoming time frame.

23. The method of claim 14, further comprising:
assigning, by the system, respective resources of available resources of the healthcare facility to the respective housekeeping tasks based on attributes associated with the respective resources that facilitate minimizing the expected turnaround times.

24. The method of claim 23, wherein the respective resources include employees and wherein the attributes include skill sets respectively associated with the employees.

25. The method of claim 14, further comprising:
determining, by the system, whether one or more of the expected turnaround times for one or more tasks of the respective housekeeping tasks fail to meet a defined turnaround time requirement for the one or more tasks; and
generating, by the device, a notification regarding failure of the one or more turnaround times to meet the defined turnaround time requirement based on a determination that the one or more turnaround times fail to meet the defined turnaround time requirement.

26. The method of claim 14, further comprising:
determining, by the system, whether available resources of the healthcare facility are sufficient to fulfill the respective housekeeping tasks within the defined upcoming time frame based on the expected demand; and
generating, by the system, a notification regarding insufficient system resources based on determination that the available resources are insufficient to fulfill the respective housekeeping tasks within the defined upcoming time frame.

27. A non-transitory machine-readable storage medium, comprising executable instructions that, when executed by a processor, facilitate performance of operations, comprising:
collecting sets of state information for a healthcare facility every predefined time interval over a course of operation of the healthcare facility, the sets of state information comprising operating conditions data regarding operating conditions of the healthcare facility over each predefined time interval and task data regarding pending housekeeping tasks and performed housekeeping tasks over each predefined time interval;
regularly retraining one or more demand forecasting models using the sets of state information and a first machine learning process to forecast future demands for housekeeping tasks of the healthcare facility based on changes in the operating condition data and the task data; and
regularly retraining one or more turnaround round time forecasting models using the sets of state information and a second machine learning process to forecast expected turnaround times for completing the housekeeping tasks based on the changes;
employing the one or more demand forecasting models to estimate, every predefined time interval, an upcoming expected demand for an upcoming group of housekeeping tasks of the healthcare facility for performance over a defined upcoming time frame based on a most recently collected set of the sets;
employing the one or more turnaround time forecasting models to estimate, every predefined time interval, upcoming expected turnaround times for completing respective housekeeping tasks of the upcoming group over the defined upcoming timeframe based on the most recently collected set; and
determining a prioritization framework for performing the respective housekeeping tasks of the upcoming group based on the upcoming expected demand and the upcoming expected turnaround times.

28. The non-transitory machine-readable storage medium of claim 27, wherein the regularly retraining comprises retraining the one or more demand forecasting models and the one or more turnaround time forecasting models in a cyclic manner in accordance with sequential training cycles and using a group of the sets received after a previous training cycle of the sequential training cycles.

29. The non-transitory machine-readable storage medium of claim 27, wherein the first machine learning process and the second machine learning process respectively comprise an unsupervised machine learning process.

30. The non-transitory machine-readable storage medium of claim 27, the operations further comprising:
allocating available resources of the healthcare facility to the respective housekeeping tasks based on the expected demand and the expected turnaround times.

* * * * *